United States Patent [19]

Ranalletta et al.

[11] Patent Number: 5,437,283
[45] Date of Patent: Aug. 1, 1995

[54] ENDOSURGICAL ULTRASONIC PROBE WITH INTEGRATED BIOPSY ACTUATOR

[75] Inventors: Joseph V. Ranalletta, Englewood; Dennis R. Dietz, Littleton; Clyde G. Oakley, Englewood, all of Colo.

[73] Assignee: Tetrad Corporation, Englewood, Colo.

[21] Appl. No.: 228,507

[22] Filed: Apr. 15, 1994

Related U.S. Application Data

[63] Continuation-in-part of Ser. No. 989,515, Dec. 11, 1992, Pat. No. 5,335,663.

[51] Int. Cl.$^6$ ............................................. A61B 8/12
[52] U.S. Cl. ............................................. 128/662.06
[58] Field of Search .............. 128/662.03, 662.05, 128/662.06, 661.01, 660.1, 660.03

[56] References Cited

U.S. PATENT DOCUMENTS

| | | | |
|---|---|---|---|
| 4,155,258 | 5/1979 | Engeler et al. | 73/626 |
| 4,417,583 | 11/1983 | Bechai et al. | 128/660 |
| 4,469,106 | 9/1984 | Harui | 128/662.05 |
| 4,593,699 | 6/1986 | Poncy et al. | 128/660 |
| 4,646,722 | 3/1987 | Silverstein et al. | 128/4 |
| 4,699,154 | 10/1987 | Lindgren | 128/754 |
| 4,763,662 | 8/1988 | Yokoi | 128/660 |
| 4,815,470 | 3/1989 | Curtis et al. | 128/662.03 |
| 4,817,616 | 4/1989 | Goldstein | 128/662.06 |
| 4,907,395 | 3/1990 | Opie et al. | 53/434 |
| 4,911,173 | 3/1990 | Terwilliger | 128/662.06 |
| 4,944,308 | 7/1990 | Akerfeldt | 128/751 |
| 4,951,677 | 8/1990 | Crowley et al. | 128/662.06 |
| 4,953,558 | 9/1990 | Akerfeldt | 128/751 |
| 4,958,625 | 9/1990 | Bates et al. | 128/754 |
| 4,997,084 | 3/1991 | Opie et al. | 206/364 |
| 5,002,059 | 3/1991 | Crowley et al. | 128/4 |
| 5,025,778 | 6/1991 | Silverstein et al. | 128/4 |
| 5,088,178 | 2/1992 | Stolk | 29/453 |
| 5,090,414 | 2/1992 | Takano | 128/662.05 |
| 5,121,749 | 6/1992 | Nassi et al. | 128/692 |
| 5,121,751 | 6/1992 | Panalletta | 128/754 |
| 5,131,393 | 7/1992 | Ishiguro et al. | 128/660.09 |
| 5,135,001 | 8/1992 | Sinofsky et al. | 128/662.06 |
| 5,161,542 | 11/1992 | Palestrant | 128/754 |
| 5,190,045 | 3/1993 | Frazin | 128/662.06 |
| 5,235,987 | 8/1993 | Wolfe | 128/662.05 |
| 5,284,156 | 2/1994 | Schramm et al. | 128/754 |

OTHER PUBLICATIONS

General Purpose Pro/Covers TM, Advertising Brochure, Civco, date unknown.
AI 5200 Ultrasound Imaging System, Advertising Brochure, Acoustic Imaging, Tempe, Arizona, date unknown.
OR340 Intraoperative Ultrasound System, Advertising Brochure, Codman & Shurtleff, Inc., a Johnson & Johnson Company, Randolph, Mass., date unknown.
"For Exceptional Clinical Versatility", Aloka, Date Unknown.
"Laparoscope Probe", Advertising Sheet, Vermon, Date Unknown.
"Biopsy Needle Guides", Civco, Date Unknown.

*Primary Examiner*—George Manuel
*Attorney, Agent, or Firm*—Sheridan Ross & McIntosh

[57] ABSTRACT

A medical endosurgical device is provided having both ultrasonic imaging and biopsy capabilities for easy grasping and manipulation by a surgeon. The medical endosurgical apparatus includes an ultrasonic imaging probe having an insertion portion with an ultrasonic device near the insertion tip and a probe handle for manipulating the ultrasonic imaging probe to position the ultrasonic device in the patient's body. The medical endosurgical device also includes a biopsy actuator that is mounted on the handle of the ultrasonic imaging probe so that a biopsy needle assembly exiting from the biopsy actuator is oriented to the field of view of the ultrasonic device on the probe. The medical endosurgical apparatus may also include a rigid sheath disposed over the insertion portion of the ultrasonic imaging probe that is engaged with and oriented to the ultrasonic imaging probe such that a biopsy needle assembly passing through a lumen in the rigid sheath would be oriented to the field of view of the ultrasonic device.

35 Claims, 21 Drawing Sheets

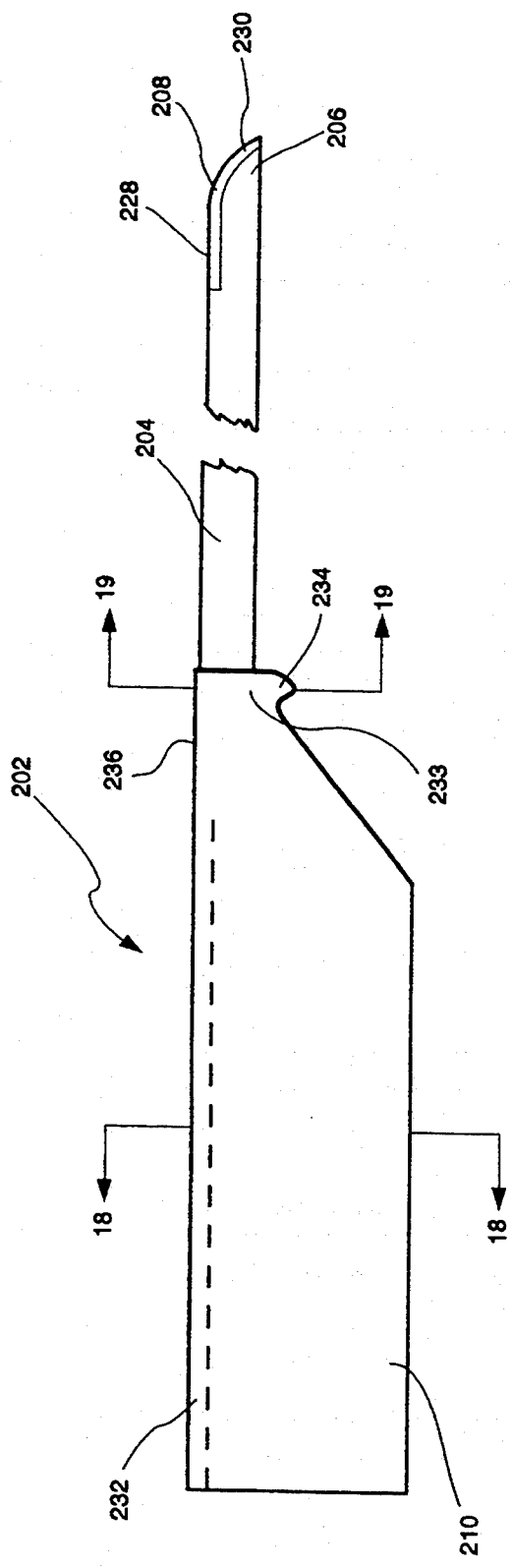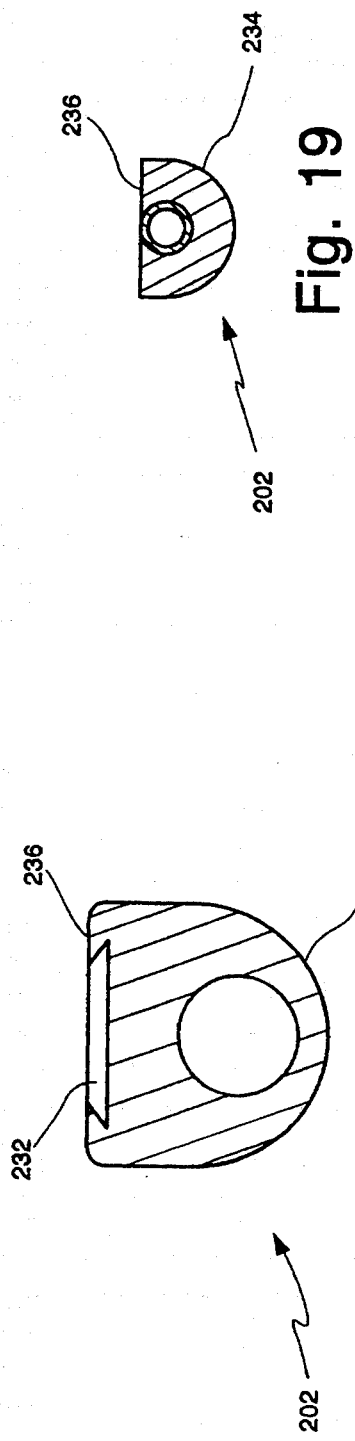
Fig. 17
Fig. 18
Fig. 19

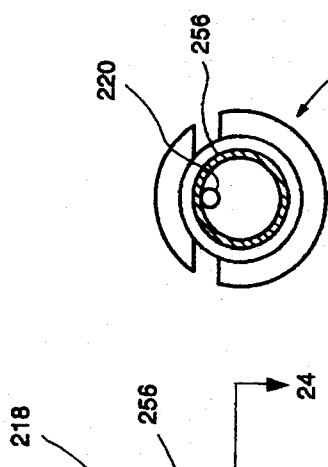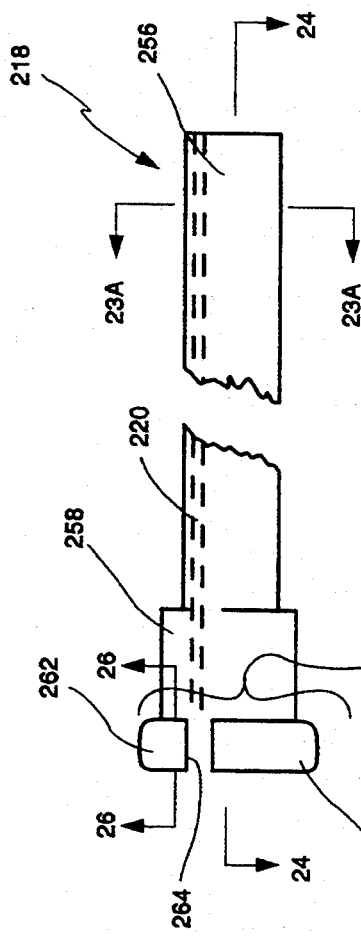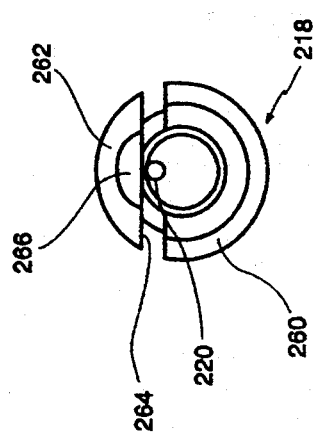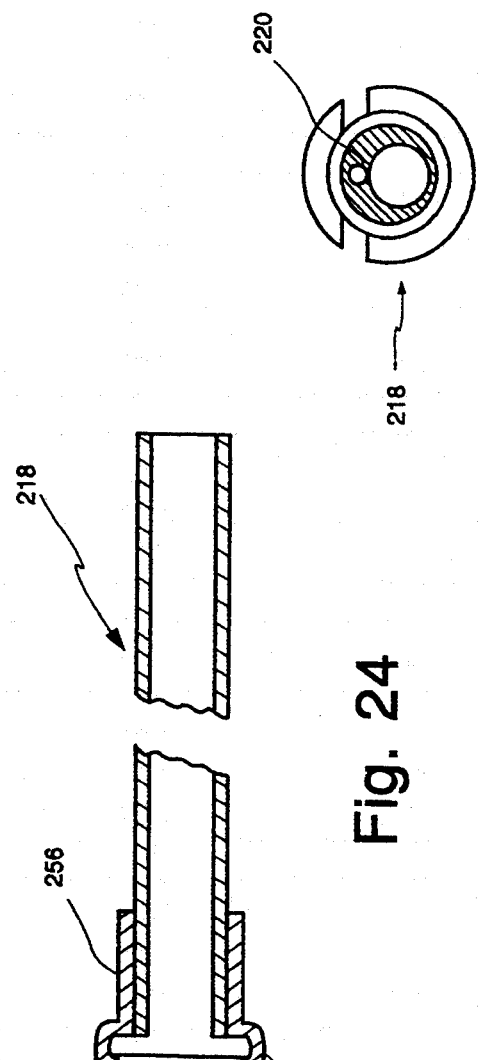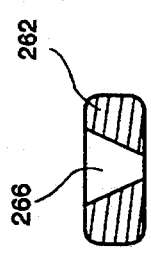

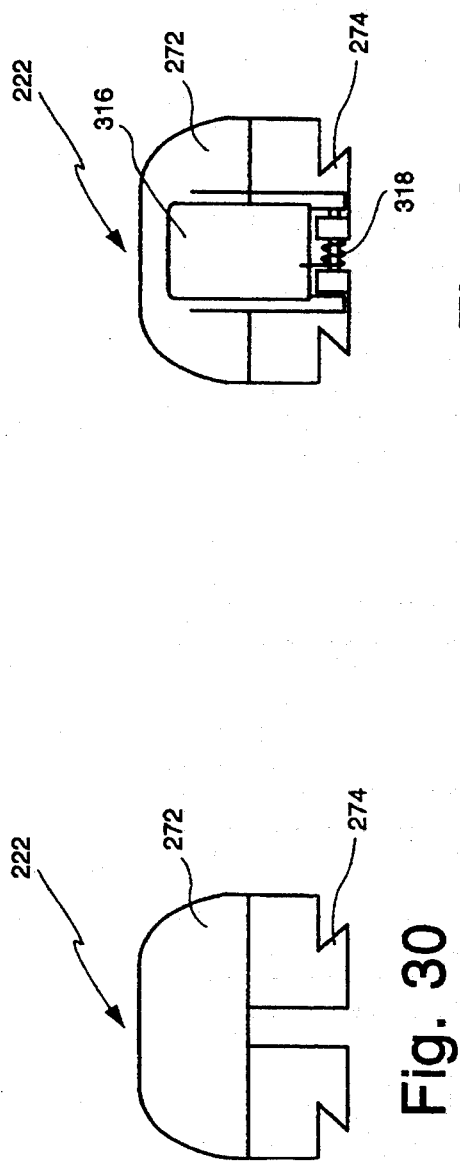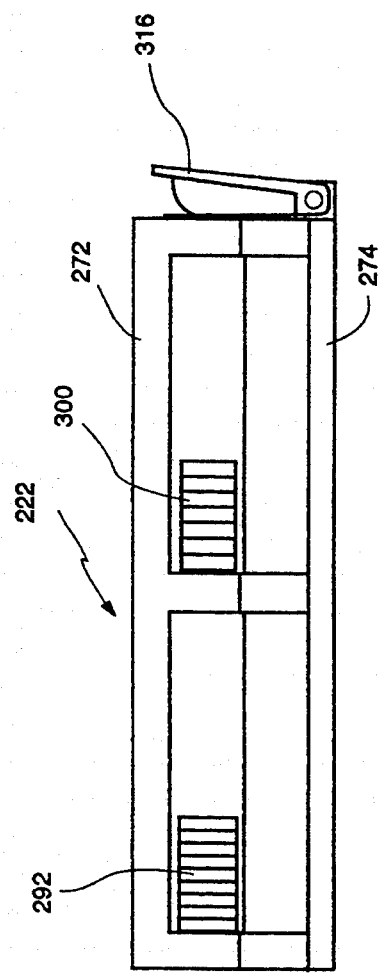

ENDOSURGICAL ULTRASONIC PROBE WITH INTEGRATED BIOPSY ACTUATOR

CROSS REFERENCE TO RELATED APPLICATIONS

This application is a continuation-in-part of U.S. patent application Ser. No. 07/989,515 by Oakley et al. filed Dec. 11, 1992 now U.S. Pat. No. 5,335,663.

FIELD OF THE INVENTION

The present invention relates to medical surgical apparatus that are particularly suited for use in endosurgery.

BACKGROUND OF THE INVENTION

Ultrasonic imaging has found several applications in the medical field, especially to view internal anatomical tissue and structures. One well known application, for example, is to use a hand held ultrasonic probe to image a developing fetus during pregnancy. Ultrasonic imaging has also found application in laparoscopic surgery, such as in the performance of biopsies and excision of internal organs or other tissue.

Endosurgery involves the use of small diameter tools that are inserted into a patient's body through a small, unnatural hole or surgical port, that is established by puncturing the external tissue of an organ, such as the skin. As used herein, endosurgery includes all surgical operations performed through a surgical port, including laparoscopic, thorascopic, pelviscopic and extraperitoneal surgical approaches. By way of example, specific discussions of laparoscopic operations are used hereinafter. It should be recognized, however, that the discussions concerning laparoscopic operations apply equally to other forms of endosurgery, including thorascopic, pelviscopic, and extraperitoneal operations. In laparoscopic surgery, the hole is made by puncturing the abdominal wall with a sharp edged instrument called a trocar. A small working tube, called a cannula, is then inserted into the hole to hold it open. Through the internal passageway of the cannula, referred to as a surgical port, are passed the necessary instruments into the body cavity to perform desired surgical operations.

Normally, the trocar and cannula are configured in a single structure. Also, the cannula is usually fitted inside with some type of sealing apparatus, such as, for example, a flapper valve that can be forced open by a tool entering through the cannula, and which springs closed to seal the internal passageway through the cannula when not in use. The cannula can also be fitted with annular sealing devices for sealing between a probe inserted through the cannula and the inside wall of the cannula. Such a means for sealing the passageway of the cannula prevents contaminants from the outside environment from invading the body cavity, thereby reducing the possibility of infection.

Various probes have been used to aid laparoscopic surgical operations. For example, optical probes are often used to view the outer surfaces of internal organs. Also, ultrasonic probes have been used to assist in viewing the internal structures of organs to obtain information that may be necessary for performance of certain surgical operations. For example, a surgeon might need to be able to identify and distinguish the cystic duct from the common duct in the gall bladder/liver to perform certain procedures.

One common laparoscopic procedure is a biopsy, in which a sample of tissue is taken from inside a patient's body. Presently, the taking of a biopsy involves the manipulation and coordination of several probes. Typically, a video television probe is inserted into the patient. The video probe is used to provide the surgeon with a picture of the surface tissue of various structures within the patient. In many cases, an ultrasonic probe is also inserted into the patient to obtain an ultrasonic image of the tissue underlying the surface tissue identified with the visual probe. After locating the underlying tissue of interest, a biopsy needle is then inserted into the patient's body. The surgeon directs the tip of the biopsy needle to the underlying tissue of interest using the ultrasonic image and video image for reference. Once the biopsy needle is positioned in the proper location near the tissue of interest, then the biopsy needle is fired by a biopsy gun located outside of the patient's body. Throughout the positioning of the biopsy needle in the patient's body and the firing of the biopsy gun, the surgeon must coordinate manipulation and positioning of the ultrasonic probe and/or the video probe with one hand and the biopsy gun with the other hand, while simultaneously viewing the ultrasonic image of the tissue of interest and/or the video image. Accurately manipulating and positioning the ultrasonic probe, video probe and the biopsy gun while concentrating on the noted images is difficult. Therefore, there is significant risk that the surgeon will sample the wrong tissue, thereby requiring an additional biopsy procedure to obtain a sample of the proper tissue.

A need exists for laparoscopic surgical medical apparatuses that reduce the risks of a surgeon taking samples of the wrong tissue.

A variety of ultrasonic probes have been used in laparoscopic procedures. One type of probe has a single transducer that is mechanically moved through an arc to transmit or receive ultrasonic signals over a pie-shaped area. Such a mechanical sector scanner can be positioned on a probe to image in either a forward or a side direction. A second type of ultrasonic probe that is used to transmit or receive ultrasonic signals over an area contains several transducer elements arranged in an array. One type of array probe that has been used contains several transducers arranged in a line along the side of a cylindrically shaped probe. Such a linear array provides side imaging capability. Another type of array probe aligns the array of transducer elements along a curve at or near the end of a probe to provide forward looking capability. Such a curved array transmits and receives ultrasonic signals over a pie-shaped area like the mechanical sector scanner. Although working well for forward viewing that is useful as a general directional and positional guide, curved arrays are not well suited for imaging near the probe, as is often desirable during surgery, because of a limited field of imaging in the region near the curved array.

During laparoscopic surgical operations, ultrasonic imaging in a forward direction beyond the end of the probe is often required. Ultrasonic imaging to the side of the probe, however, is also often required. The ability to do both forward and side imaging are desirable during some operations. For example, forward imaging can be used to determine when a probe is at the location in the body cavity for side imaging organs or other tissue of interest which cannot be adequately viewed with a forward imaging probe.

Typically, when a need exists for both forward and side imaging, two separate probes are used, one for forward imaging and one for side imaging. For example, a forward imaging probe might first be inserted so that a surgeon can determine the proper distance into the body cavity at which the operation is generally to be performed and possibly also to locate an organ or other tissue of interest. The forward imaging probe is then removed and a side imaging probe is inserted to obtain a better view of the organ or other tissue of interest in preparation for a medical operation that is to be performed on the tissue, such as excising tissue or taking a biopsy sample. The use of two probes, however, is awkward. It is difficult for a surgeon performing a complex operation to mentally reorient between the forward and side looking images. Also, assuring proper repositioning of the probe at the proper distance into the body cavity can present a problem.

One attempt to provide some degree of both forward and side looking capability in a single probe has been to place a linear array at some acute angle relative to the longitudinal axis of the probe. Such an angled array, however, provides limited imaging capability in either the forward or the side directions, and is, therefore, of limited practical utility.

Another attempt to provide some degree of both forward and side looking capability in a single probe has used a mechanically scanned ultrasonic transducer. These probes, like the probes using the angled array, have proved to be of limited practical utility due to their limited imaging capability in the forward and side directions. Moreover, the moving parts associated with mechanical scanners render the probes more susceptible to malfunction.

Based on the foregoing, there is a need for an ultrasonic probe that addresses the noted deficiencies of presently known probes in providing both forward and side imaging capability.

Presently, ultrasonic images produced by ultrasonic medical probes are displayed on a video monitor with a fixed frame of reference. The image is typically displayed on the monitor from top to bottom, with the distance away from the ultrasonic probe increasing going down the screen. Therefore, tissue nearest the ultrasonic probe is displayed at the top of the monitor and tissue farthest from the probe appears at the bottom of the monitor.

A surgeon, or other medical professional, viewing the ultrasound image must mentally translate the image as displayed on the monitor to a frame of reference in the patient's body, thereby orienting the image in order to properly locate organs or other tissue of interest. Also, when the probe is moved from one position to another, or rotated to image in a different plane, the surgeon must also mentally reorient that new image relative to the old image. For example, if the surgeon is viewing a first ultrasonic image with the probe in a first position looking sideways and then rotates the probe counterclockwise to produce a second image, the surgeon must mentally translate the second image counterclockwise from the first image to properly conceptualize the patient's anatomy. These mental translations and orientations of images can be difficult to make as well as potentially distracting during complex surgical operations.

Consequently, there exists a need to provide the surgeon with an ultrasonic image that reduces the mental image translations that the surgeon must presently make each time the probe is moved to obtain a new image.

Many laparoscopic surgical operations require cutting, or excision, of internal tissue. The tissue to be cut as well as other internal structures must be located and properly identified prior to performing the cutting operation. For example, it may be necessary to locate and identify the common duct that runs through the liver so that a subsequent cutting operation on the liver will not nick or sever the duct.

Presently known methods for performing cutting operations during laparoscopic surgery use techniques for locating and identifying tissue that present significant potential for cutting the wrong tissue. For instance, one method for locating, identifying, and cutting tissue involves inserting an ultrasonic probe into the patient's body cavity to locate and identify the tissue to be cut and internal structures to be avoided. The ultrasonic probe is then removed and a surgical instrument is inserted and positioned to perform the cutting based on the information obtained from the ultrasonic probe. Positioning the surgical tool to properly perform the desired cut, however, based upon the information provided by the ultrasonic probe may be difficult, and it is possible that an improper cut can be made.

Therefore, a need exists for reducing the possibility that an improper cut or excision is made.

One problem often encountered with performing ultrasonic scans during laparoscopic operations is establishing good ultrasonic contact between ultrasonic transducers and tissue, the underlying structure of which is to be imaged. Good ultrasonic images can be produced only if adequate ultrasonic contract, often referred to as coupling, can be made between the tissue and ultrasonic transducers. Obtaining such ultrasonic contact is often difficult. For example, an ultrasonic device may be on the side of a probe, but only the tip of the probe can be contacted with the tissue of interest. Or, for example, it may be possible to contact the ultrasonic device and the tissue of interest, but in so doing the tissue is physically distorted and, therefore, the ultrasound image produced may be misleading.

One approach that has been used to establish ultrasonic contact with tissue is to fill the body cavity space in which the tissue resides with an ultrasonically transmissive fluid, such as water. However, this technique results in large amounts of transmissive fluid invading the body cavity. Transmissive fluids placed in the body cavity must normally be removed following the ultrasonic imaging operation. Assuring that large amounts of transmissive fluid have been completely removed from the body cavity can be troublesome.

Another problem with laparoscopic probes is that they are difficult to sterilize. One attempt to resolve the sterilization problem has been to place a sterile disposable cover, or sheath, over the laparoscopic probe prior to insertion of the probe into a body cavity. After removal of the probe, the sheath is discarded. As a consequence, the need for extensive sterilization of the probe is reduced.

One type of sheath that has been used to cover laparoscopic probes is a loose fitting, thin-walled, highly flexible prophylactic sheath made of an elastomeric-type material, such as latex rubber. One problem with the loose fitting prophylactic sheath however, is that it tends to catch and bind in the seals and/or a flapper valve in the cannula thereby inhibiting insertion and extraction of the probe. In extreme cases, the prophylactic sheath may tear, thereby defeating the very purpose of the sheath in providing a sterilized surface.

Another type of sheath that has been used is a thin-walled, tightly fitting, highly flexible sheath made of elastomeric-type material, such as latex rubber. The sheath is fitted on the probe by first inflating the sheath, like a balloon, and then inserting the probe into the inflated sheath. The sheath is then deflated to tightly fit around the probe. Because of the thin-walled, highly flexible nature of the sheath, however, there is still potential for binding in the cannula. Also, the procedure of fitting the sheath onto a probe is time consuming and awkward in the surgical environment. One related problem with using the sheaths just discussed, is assuring that an ultrasonically transmissive circuit is established between the ultrasonic device and the sheath. Currently, ultrasonic coupling between the ultrasonic device and the sheath is established by coating the probe with an ultrasonically transmissive fluid before covering the probe with a sheath. This procedure, however, is inconvenient, time consuming and awkward in the environment of an operating room.

Based on the foregoing, there is a need for establishing an ultrasonic device that can ultrasonically couple the transducer to the tissue of interest that avoids or reduces the problems associated with using large amounts of ultrasonically transmissive material to establish the requisite coupling.

SUMMARY OF THE INVENTION

One aspect of the present invention addresses the need for providing ultrasonic imaging capability and biopsy capability in a manner to simplify the taking of an accurate biopsy sample during endosurgery. In one embodiment, the apparatus comprises an endosurgical ultrasonic imaging probe having an ultrasonic device that is located on a portion of the probe which is inserted through a surgical port and is used to ultrasonically image tissue in a patient's body. Physically interconnected to the probe handle is an automated biopsy gun for actuating a biopsy needle assembly to take a biopsy sample with a needle tip of the biopsy needle assembly. In one embodiment, the probe handle and biopsy gun are interconnected and, together, have a contoured shape that permits a surgeon to comfortably grasp and manipulate both the probe handle and the biopsy gun with one hand, thereby reducing the number of separate surgical instruments that the surgeon must keep track of during a biopsy.

In another embodiment, the automated biopsy gun is interconnected to the handle of the ultrasonic imaging probe by a slot located on one of the probe handle and the automated biopsy gun and a rail located on the other of the probe handle and the automated biopsy gun, facilitating easy connection and disconnection of the automated biopsy gun with the probe handle. The biopsy actuator device physically interconnected to the handle of the ultrasonic imaging probe with such a slot/rail engagement can be moved longitudinally along the probe handle to accommodate longitudinal placement of a biopsy needle tip relative to an ultrasonic device in a patient's body. Because the automated biopsy gun is not permitted by the slot/rail engagement to move laterally relative to the probe handle, however, the biopsy needle tip remains aligned with the imaging plane of the ultrasonic device in the patient's body. In one embodiment, the automated biopsy gun has a locking mechanism that locks the biopsy gun in place on the handle of the ultrasonic imaging probe. The locking mechanism allows the surgeon to fix the relative positions of the ultrasonic imaging probe and the biopsy gun once the needle tip of the biopsy needle assembly has been properly positioned relative to the ultrasonic device, thereby preventing the biopsy needle tip from moving while the surgeon prepares for and takes a biopsy sample using the biopsy gun.

In another embodiment, the biopsy gun includes cocking grips mounted in pairs on opposite sides of the automated biopsy gun to facilitate cocking of the biopsy gun. For example, the opposing cocking grips permit the surgeon to obtain a firm grip for cocking the biopsy gun without moving the ultrasonic imaging probe and the biopsy needle tip that has been properly positioned to take a biopsy sample.

In one embodiment, the ultrasonic imaging probe has a keyed structure for use in holding a rigid sheath in place that may be fitted over the insertion portion of the ultrasonic imaging probe. In another embodiment, the rigid sheath is connected to the ultrasonic imaging probe with a keyed engagement shape so that a lumen through the rigid sheath is oriented to the imaging plane of the ultrasonic device. A surgical tool, such as a biopsy needle assembly, passing through the lumen is thereby oriented so as to pass within the imaging plane of the ultrasonic device upon exiting the lumen.

In another aspect, the present invention provides an ultrasonic imaging probe having both forward and side imaging capabilities on a single probe. The probe comprises a carrier and an array of ultrasonic transducers capable of imaging in a forward direction beyond the end of the end portion of the probe that is inserted into the patient's body. The ultrasonic array includes a first array portion that includes at least one ultrasonic transducer oriented to image at an acute angle relative to the longitudinal axis of the carrier such that the transducer images in a forward direction beyond the end of the probe. The array also includes a second portion having a plurality of ultrasonic transducers arranged in a substantially linear fashion and substantially parallel to the longitudinal axis of the carrier for side imaging.

In a further embodiment, the first array portion includes a plurality of transducers that are oriented so as to define a substantially planar curve, i.e., a curve that lies substantially in a single plane. In one embodiment, the planar curve has a large radius of curvature that extends over an acute included angle, thereby facilitating manufacture of the probe by making electrical connections to individual transducer elements easier to make. Alternatively the planar curve can have an increasing radius of curvature. By having a large radius of curvature, thereby decreasing the angle in which the curve is included, or by having an increasing radius of curvature, additional room is provided to make electrical connections to individual elements over the length of the curve. This can be particularly advantageous when the radius of the carrier is very small, such as with instruments used in laparoscopic surgery.

In a still further embodiment, the carrier of the probe is substantially cylindrical over much of its length, with the substantially circular cross section defining the areal boundary, perpendicular to the longitudinal axis, within which all portions of the probe must lie. In one embodiment, the transducer elements of the second array portion, arranged substantially in a line parallel with the longitudinal axis, are recessed relative to the areal boundary, thereby permitting other surgical tools, such as a biopsy needle, to be located within or passed through the recess. Moreover, those other surgical tools can be positioned within the imaging field of the linear portion of the array, thereby allowing a surgeon to simultaneously obtain an image of both the body tissue of interest and the surgical tool.

Another embodiment of the invention provides an ultrasonic imaging apparatus that addresses the mental translations and reorientations that surgeons must make with respect to the display of present ultrasonic images. The ultrasonic imaging apparatus includes an ultrasonic probe with at least one ultrasonic element that transmits a first electrical signal, representative of a received ultrasonic signal, a position sensor that produces a second electrical signal representative of the position of the probe, a processor for constructing a video image of the ultrasonic signal for display on a video monitor from the first electrical signal and manipulating the video image using the second electrical signal to reflect the orientation of the ultrasound image. For example, a first video image could be displayed on a video monitor representing an ultrasound image produced at a first position with a side imaging ultrasound probe. The probe could then be rotated counterclockwise to a second side imaging position. The second video image is rotated counterclockwise on the video monitor relative to the first video image thereby relieving the surgeon from having to make the mental adjustment in the image. In one embodiment, both a rotational position sensor and a translational position sensor are provided so that both rotations and translations of images can be effected.

Yet another embodiment includes a device for establishing a reference point for the position sensor that relates to a patient's body so that the ultrasound image displayed on a video monitor can be oriented to the patient. For example, if the reference point is the patient's head, the position sensor can produce data that allows a video image to be constructed in which the top of the video monitor corresponds to the patient's head and the bottom of the video monitor corresponds to the patients feet, regardless of the direction in which the ultrasonic probe is imaging.

One embodiment of the invention is directed to the problem locating or identifying the tissue of interest and then performing a cutting or other surgical operation. In an embodiment, the invention provides a laparoscopic probe that includes both a surgical device for cutting and/or cauterizing tissue and an ultrasonic device with a field of imaging that either includes the surgical device or is immediately adjacent to the surgical device. Because the surgical device is integral with the probe containing the ultrasonic device and is proximately located to the ultrasonic device, the surgeon is less likely to make improper cuts. In one embodiment, the surgical device includes an electrocautery hook that is positioned within or adjacent to the ultrasonic field of imaging of an ultrasonic array. Using the ultrasonic image, a surgeon can locate and identify the proper tissue for cutting as well as the internal structures that are not to be cut. After locating the proper tissue, the surgeon can activate the electrocautery hook and, because of the overlapping or immediately adjacent field of imaging, can closely control the precise position at which the cut is made.

A further embodiment of the present invention addresses the need to establish ultrasonic contact between an ultrasonic device and tissue of interest. The apparatus comprises a carrier, an ultrasonic device mounted on the carrier, and a device for use in injecting an ultrasonically transmissive medium adjacent to the ultrasonic device. The transmissive medium is placed in the vicinity of the ultrasonic device for the purpose of establishing an ultrasonic circuit, or bridge, with the tissue that is located in the field of view of the ultrasonic device.

In one embodiment, a high viscosity fluid is used as the transmissive medium. High viscosity fluids have the advantage that the medium has a reduced tendency, relative to lower viscosity fluids, to disperse or flow away from an area immediately adjacent to the ultrasonic device. Consequently, a relatively small amount of such high viscosity fluid can be used to provide the necessary ultrasonic contact for imaging the tissue of interest. The result is that a relatively small amount of transmissive medium is used which is relatively easy to remove from the body following ultrasonic imaging. Ease of removal is facilitated by the small amount of medium and an increased tendency of high viscosity medium to remain in the vicinity of the ultrasonic device. In one embodiment, the transmissive medium adheres to the outer surfaces of the carrier and ultrasonic device and does not disperse or flow away from that immediate vicinity.

One embodiment of the present invention provides a disposable sheath for covering a probe that is to be inserted into a patient's body cavity. In one embodiment, the sheath is a rigid structure that substantially reduces, or eliminates, any problem with binding of the sheath in the cannula as has been experienced with the thin walled, highly flexible, elastomeric-type sheaths of the prior art.

Another embodiment of the sheath includes a chamber within the sheath. The chamber contains an ultrasonically transmissive medium and is sealed with a breakable membrane. When a probe is inserted into the sheath, the probe breaks the membrane and the ultrasonic device of the probe enters the chamber containing the ultrasonically transmissive medium. An ultrasonic circuit is thereby established between the ultrasonic device and the sheath.

Another embodiment of the sheath includes an inflatable balloon at or near a first terminal end of the sheath that is inserted into the patient's body cavity. The balloon can be inflated with an ultrasonically transmissive medium to establish an ultrasonic circuit between an ultrasonic device of the probe inserted into the sheath and tissue to be ultrasonically scanned.

Another embodiment of the sheath is shaped to establish a desired orientation between the ultrasonic probe and the sheath. Orientation is such that the ultrasonic device of the probe is always adjacent to one or more lumens through which ultrasonically transmissive medium can be transmitted to and injected immediately adjacent the sheath in the direction of the ultrasonic beam. An ultrasonic circuit between the sheath and tissue of interest is established by the excreted medium.

BRIEF DESCRIPTION OF THE DRAWINGS

FIG. 17 is a side view of one embodiment of an ultrasonic imaging probe;

FIG. 18 is a sectional view of the handle of one embodiment of an ultrasonic imaging probe;

FIG. 19 shows a sectional view of a keyed engagement shape for engaging a rigid sheath of one embodiment of an ultrasonic imaging probe;

FIG. 22 is a side view of one embodiment of a rigid sheath;

FIG. 23A is a sectional view of one embodiment of a rigid sheath showing a lumen inside the sheath;

FIG. 23B is a sectional view of one embodiment of a rigid sheath showing a lumen in the wall of the rigid sheath;

FIG. 24 is a sectional view of one embodiment of a rigid sheath showing a connection clip in the shape of a hollow lip;

FIG. 25 is an end view of one embodiment of a rigid sheath showing a keyed engaging shape for engaging an ultrasonic imaging probe;

FIG. 26 is a sectional view of an orientation guide on one embodiment of a rigid sheath;

FIG. 29 is a side view of one embodiment of a biopsy actuator;

FIG. 30 is a front end view of one embodiment of a biopsy actuator;

FIG. 31 is a back end view of one embodiment of a biopsy actuator;

DETAILED DESCRIPTION

In one aspect, the present invention is an endosurgical ultrasonic probe that provides ultrasonic imaging both in a forward direction past the end of the probe that is inserted into a patient's body and also to the side of the probe. The probe is particularly suited for use in laparoscopic, thorascopic, pelviscopic and extraperitoneal surgical operations.

Figure 1A:
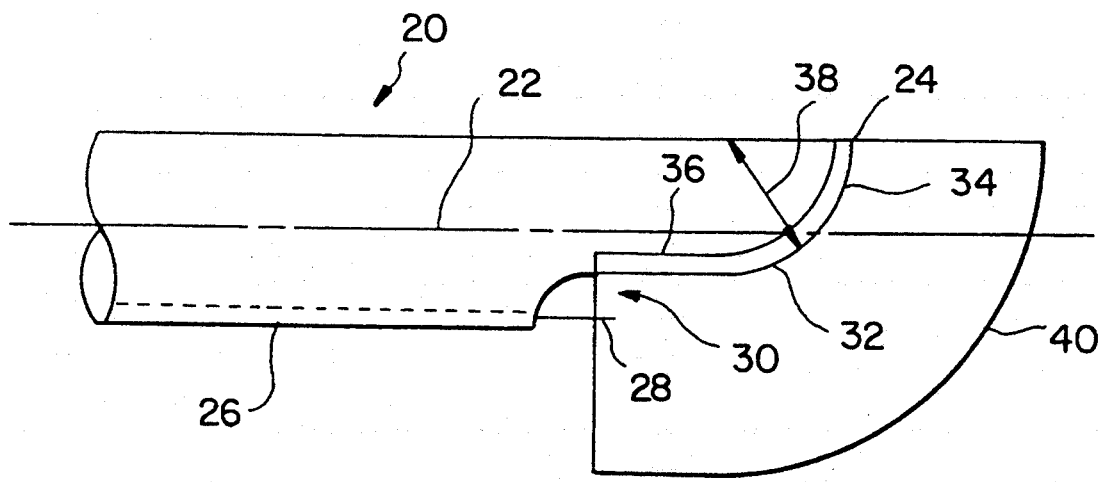
FIGS. 1A and 1B show a side view and a top view of a probe containing a 90° curved first array portion and a linear second array portion of an ultrasonic transducer array, which second array portion is recessed to allow for passage of a surgical tool, such as a biopsy needle.
Figure 1B:
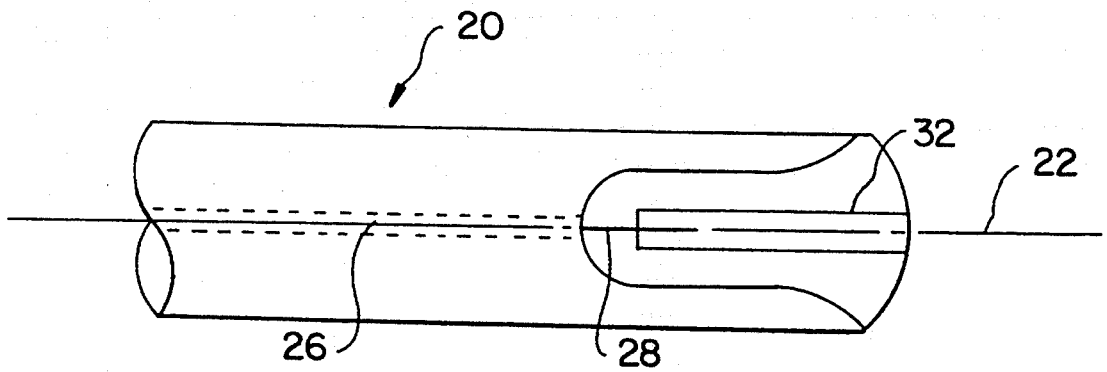

FIGS. 1A and 1B show one embodiment of a probe. Probe 20 comprises a carrier having a longitudinal axis 22 extending between a first terminal end 24, which is inserted into the patient's body, and a second terminal end, not shown, which remains outside of the patient's body. Extending through the carrier is a smaller diameter conduit 26, called a lumen, through which surgical tools, such as a biopsy needle 28, can be transmitted from outside of the patient's body to a recess area 30 near the first terminal end 24. Typically, such a carrier for a laparoscopic probe would have a maximum cross sectional width smaller than about 12 millimeters, and often from about 10 millimeters to about 12 millimeters.

The probe 20 also has an array 32 of ultrasonic transducers comprising a curved first portion 34 and a linear second portion 36. The curved portion 34 has at least one ultrasonic transducer that is situated to image at an acute angle relative to the longitudinal axis 22. Preferably, the curved portion 34 comprises a plurality of ultrasonic transducer elements arranged in a planar curve. The curved portion 34 shown in FIG. 1A is configured as a planar curve having a 90° included angle and a radius of curvature 38, as shown.

The curved portion 34 is continuous with the linear portion 36, which has a plurality of ultrasonic transducer elements located substantially in a line that is substantially parallel to the longitudinal axis 22. The linear portion 36, therefore, produces an ultrasound image directed to the side of the probe. An array having a curved first portion extending over a 90° arc and a linear second portion, as shown in FIG. 1A, has an ultrasound imaging pattern 40 extending from a full forward imaging position at one end of the curved portion 34 to a full side imaging position along the linear portion 36.

The array 32 is preferably located relative to the lumen 26 so that a surgical tool, such as a biopsy needle 28, exiting the lumen 26 will pass through the recess area 30 in such a manner that the tool passes through the field of view of the linear portion 36 of the array. If the tool exiting the lumen 26 is extended through the recess beyond the linear portion 36, such tool would also preferably pass within the field of view of the curved portion 34 of the array. This ability to pass surgical tools directly to the vicinity of the array 32 can facilitate precise placement of tools, such as biopsy needles, at the desired point as located by the ultrasonic image produced by the array 32. Preferably, the array 32 has at least about thirty-two transducer elements, more preferably at least about sixty-four transducer elements, and most preferably at least about one hundred and twenty-eight transducer elements. The relative number of transducer elements included in the curved portion 34 relative to the linear portion 36 will depend upon the specific embodiment and the relative needs for viewing beyond the first terminal end of the carrier and viewing to the side of the carrier. Frequently, however, transducer elements will be equally split between the two portions. Transducer elements are typically from about 3 mm to about 5 mm long. The individual transducer elements can be spaced at any convenient distance from each other, providing that spacing is close enough to provide adequate imaging. Frequently, transducer elements are spaced from about 0.1 mm to about 0.3 mm on center and preferably at about 0.2 mm on center, with the longitudinal axis of the transducer elements extending into the internal space of the carrier. An array with one hundred twenty-eight transducers would, therefore, be approximately one inch long as measured along the surface of the array.

Viewing beyond the first terminal end of the probe using the curved array portion 34 is desirable to help determine what organs or other tissue lie in the path of the probe, to help determine when the probe has reached the proper distance into the patient's body, and to identify organs or tissue of interest. The side looking second portion 36 is particularly suited for viewing a particular organ or other tissue once the probe has been positioned at the proper distance within the patient's body.

Figure 2A:
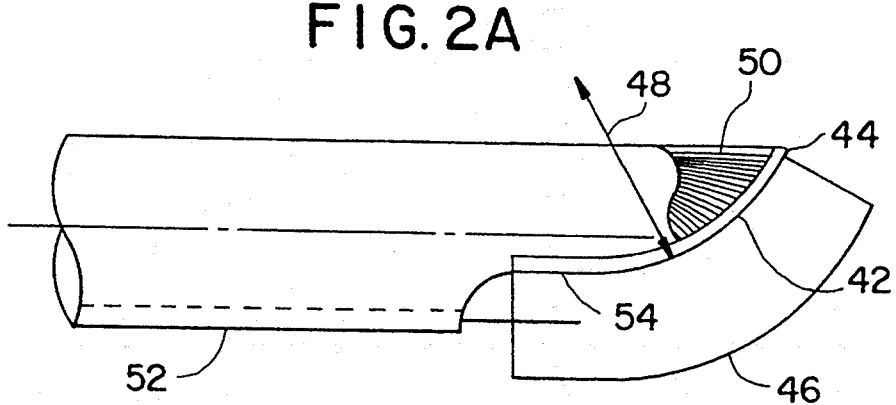
FIGS. 2A and 2B show a side view and end view of a probe having both a curved first array portion and a linear second array portion of an ultrasonic transducer array, with the curved first array portion included within an acute angle and having an enlarged radius of curvature to facilitate the making of electrical connections to individual transducer elements.
Figure 2B:
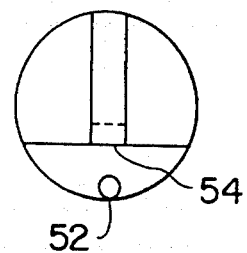

FIGS. 2A and 2B show another embodiment of a laparoscopic ultrasonic probe having features as previously described for the probe shown in FIGS. 1A and 1B, except as noted. The first portion 42 of the ultrasonic transducer array is shown as arranged in a planar curve having a larger radius of curvation than that shown in FIGS. 1A and 1B. Also, the curved portion 42 has an acute included angle. Therefore, the curved first portion 42 has a capability of imaging, as shown by the imaging pattern 46, beyond the end of the probe that is somewhat restricted relative to the 90° curved first portion 34 shown in FIG. 1A. The relatively flatter curve of the curved portion 42 relative to that shown in FIG. 1A is due to the larger radius of curvature 48 that extends well beyond the edge of the probe carrier, as shown.

The relatively flatter curve in the arc of curved portion 42, although somewhat reducing the forward viewing capability of the array, has the advantage of facilitating electrical connection of transducer wires 50 to individual transducer elements in the curved first array portion 42. Such additional space for making electrical connections to individual transducer elements can significantly decrease the cost of manufacturing the probe. As an alternative to a larger radius of curvature, an increasing radius of curvature can also be used. For example, the radius of curvature of the curved array portion could be smallest at the end of the curved portion nearest the end of the probe and could increase, thereby flattening the curve, moving along the curved portion away from the end of the probe.

The probe shown in FIGS. 2A and 2B also has a lumen 52 extending through the carrier and through which surgical tools can be transmitted to a recessed area in the vicinity of the linear second array portion 54.

Figure 3:
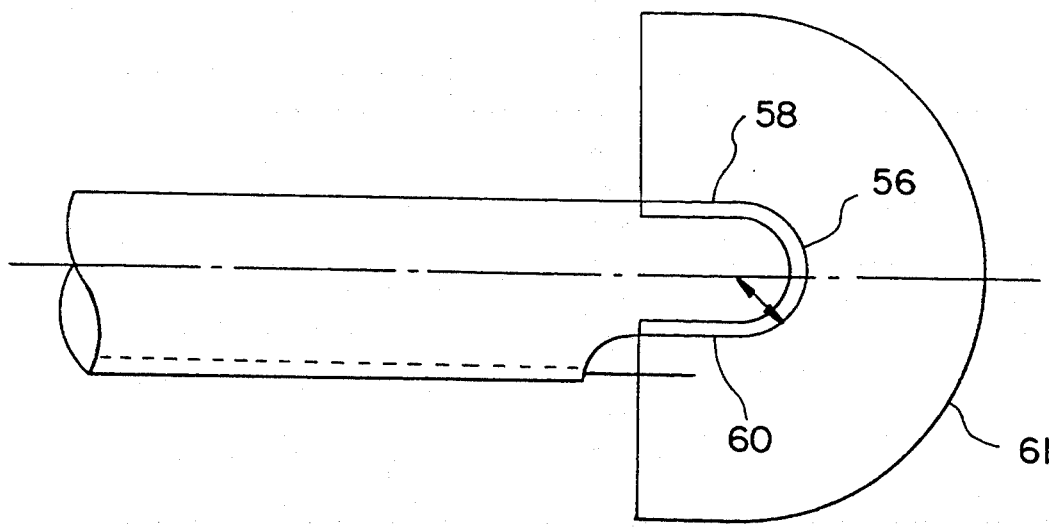
FIG. 3 shows a side view of a probe having an ultrasonic transducer array comprised of a 180° curved first array portion and two linear array portions.

FIG. 3 shows another embodiment of an ultrasonic probe for use in laparoscopic surgery. The first portion 56 of the array extends over a full semi-circle. Other configurations for the first portion that extend from one side of the probe to the other are also possible, and need not extend through a full 180°. Unlike the probes previously described, this probe contains two linear portions 58 and 60, thus providing an imaging pattern 61 extending down two sides of the probe and completely around the front of the probe.

Another aspect of the present invention involves sensing the position of an ultrasonic probe, generating an electrical signal representative of the position of the probe, and using that electrical signal to orient a video display of an ultrasonic image generated by the probe.

Figure 4:
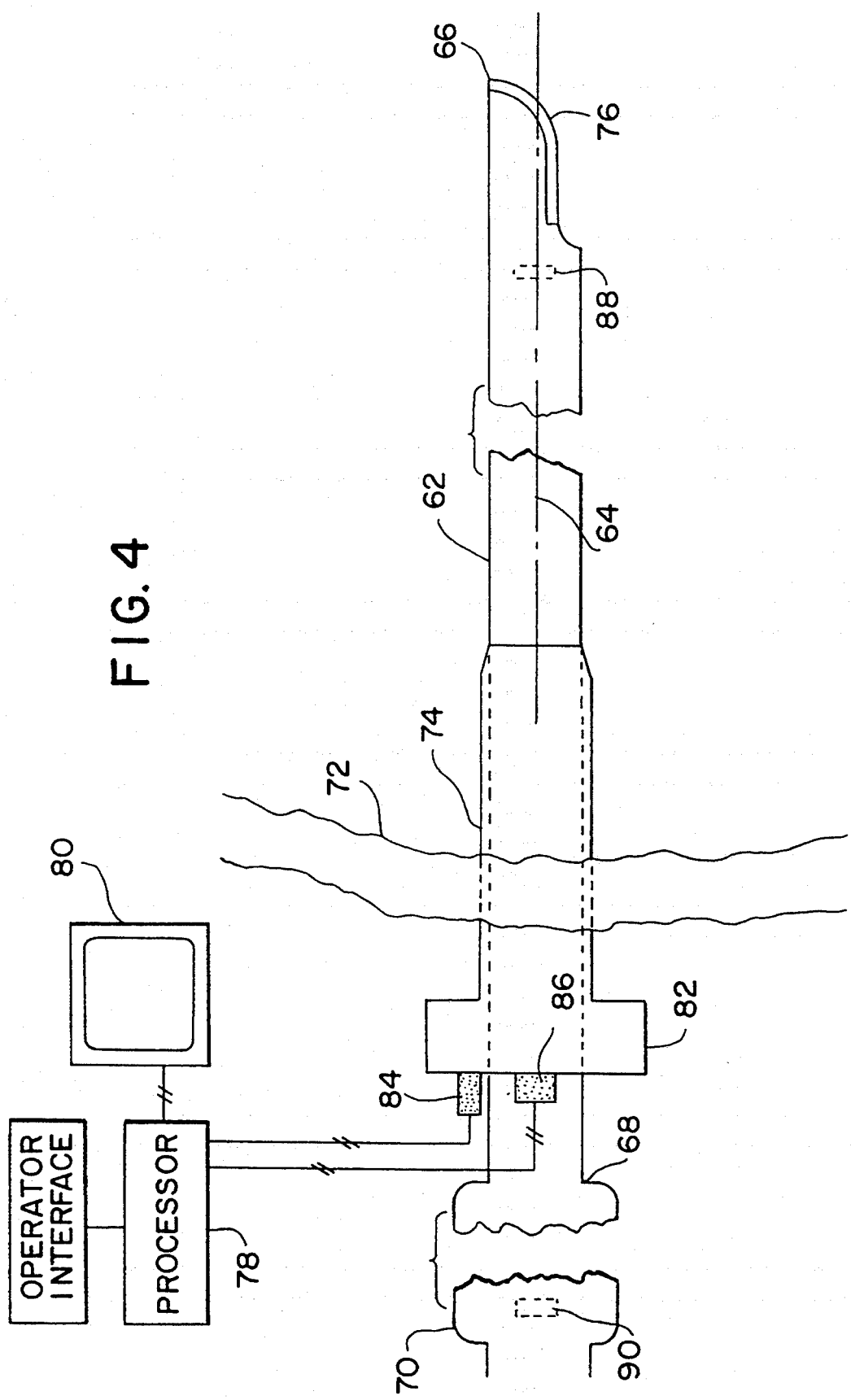
FIG. 4 shows an apparatus for use in performing ultrasonic imaging that includes translational and rotational position sensing devices for sensing the position of an ultrasonic probe and using the position information to manipulate the displayed ultrasonic video image.

FIG. 4 shows one embodiment of the invention. An ultrasonic probe 62 with a longitudinal axis 64 having a first terminal end 66 that is inserted into a patient's body and a second terminal end 68 that is connected to a handle 70, with which a surgeon would manipulate the probe. The first terminal end 66 of the probe is inserted into the patient's body through a hole in the abdominal cavity 72 that is held open by a tubular device 74, called a cannula, the internal passageway through which is often referred to as a surgical port. An array 76 having a plurality of ultrasonic transducers is located near the first terminal end 66 of the probe. The ultrasonic transducers produce first electrical signals that are applied to a processor 78 that places the signals in a form suitable for display as a video ultrasound image on a video monitor 80. Electrical circuits for the ultrasound transducers are not shown.

Mounted on the cannula adjacent to the surgical port are two position sensors 84 and 86. A first position sensor 84 monitors the translational position of the probe 62 along the longitudinal axis 64. A second position sensor 86 monitors the rotational position of probe 62 about the longitudinal axis 64.

The first positional sensor 84 generates an electrical signal representative of the translational position of the probe which goes to a processor 78 and is used to manipulate ultrasound video images formed from the signals provided by the array 76. For example, the electrical signal provided by the first positional sensor 84 can be used to generate consecutive video ultrasound images to be displayed sequentially across the video monitor in proper spacial relationship to one another in a translational direction.

The second position sensor 86 generates an electrical signal that is representative of the rotational portion of the probe which is transmitted to a processor 78 where the signal is used to manipulate and orient an ultrasound video image formed from the signals provided by the array 76 relative to the rotational position of the array 76 on the probe 62. For example, if the array 76 is imaging at a first position and is subsequently rotated to a second position in a counterclockwise direction, the ultrasound video image on the monitor 80 also rotates on the video monitor screen in a counterclockwise direction.

In one embodiment, a reference point can be set so that a particular direction on the video monitor represents a specific orientation relative to the patient. For example, if a probe is inserted through the surgical port and travels in a vertical direction into the body cavity, it may be desirable to select the top of the video monitor as corresponding to the head of the patient. If the ultrasonic array is then rotated to image in a direction towards the head, the portions of the image closest to the ultrasonic array will appear at the bottom of the video monitor and the portions of the image farthest from the array, being closer to the head, will appear at top of the video monitor. If the probe is then rotated to image in a direction towards the feet, then those portions of the image closest to the probe will be near the top of the video monitor and those portions of the image farthest from the probe will appear near the bottom of the video monitor. If the probe is positioned to look to one side, or the other, of the patient's body then portions of the image closest to the array would show near the appropriate side of the monitor.

If, however, a surgeon is inserting a probe through a surgical port that enters the body mostly from the side such that the probe travels across the body cavity, then it might be convenient for the surgeon to select the top of the screen as corresponding to the front the patient's body. The bottom of the screen would correspond to the back of the patient's body. The video image would rotate as the probe rotates, but the video image would always maintain orientation relative to the front and back of the patient, similar to orientation with the head and feet as previously described.

Positional sensors 84 and 86 can be any devices that produce electrical signals indicative of the position of the probe 62. For example, these sensors might have friction wheels that contact the probe 62 and that are coupled to opto-electronic encoders or counters that produce electrical signals. Another method of sensing position might be to put a series of dots, lines, or other marks directly on the shaft of the ultrasound probe 62 and to optically detect the motion of these marks using reflective encoders as position sensors 84 and 86.

In addition, or alternatively, to rotational position sensor 84, which is mounted at the surgical port, a rotational sensor that is sensitive to gravitational force could be placed within the probe. Preferably, such a gravitationally sensitive sensor 88 would be positioned near the first terminal end in the vicinity of the array 76. Alternatively, such a gravitationally sensitive sensor 90 could be placed in the handle 70 attached to the probe 62.

Figure 5:
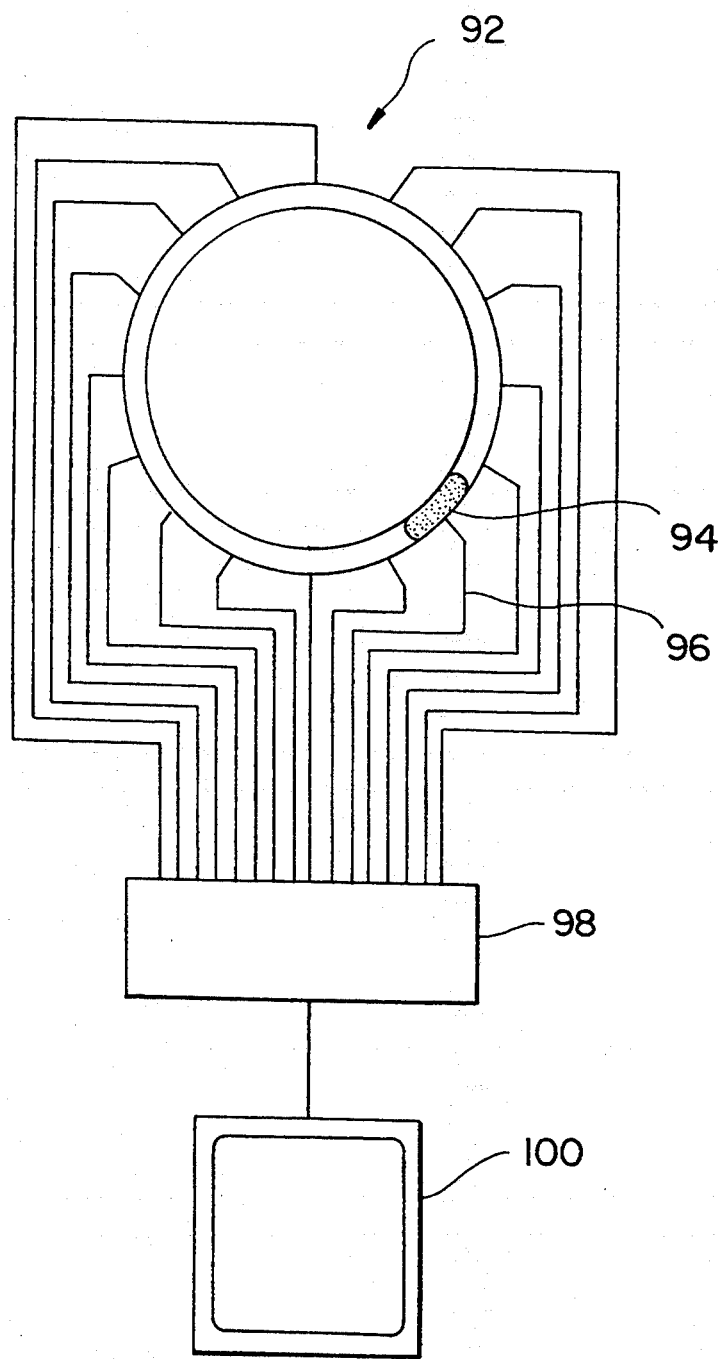
FIG. 5 shows a mercury switch that can be used to sense rotational position of a probe based on gravitational force.

One suitable gravitationally sensitive position sensor is a switch having an electrically conductive mass, such as a ball of liquid mercury or a solid metal ball, that is capable of responding to gravitational force to close one of several contacts in the switch. FIG. 5 shows a switch 92 actuated by a ball of mercury. As a probe with the mercury switch 92 is rotated, a ball of mercury 94 in mercury switch 92 moves such that the mercury is always at the position of the switch pointing in a downward direction in response to the gravitational force. The mercury switch will, therefore, complete the circuit with the contact that is pointing down and an electrical signal will be generated in the circuit completed by the contact and the electrical signal is transmitted to a processor 98 where it is used to orient an ultrasonic video display on video monitor 100. Rotation of the ultrasound video image is as described previously for rotational position sensor 84 as shown in FIG. 4.

As previously discussed, a reference point can be established for orientation of a video ultrasound image relative to the patient. The reference point for the position sensors can be established in either an absolute or a relative sense. For example, if a rotational position sensor is used that responds to gravity, then image orientation can be established with respect to actual up/down orientation. If however, the position sensor consists of either an optical or mechanical encoder, then in order to establish a reference position, the system operator would have to move the probe into a predetermined position (i.e., image plane from front to back) and then notify the system by means of a switch or contact closure, via an operator interface 101 with processor 78, that the probe is in the reference position.

In a further aspect, the present invention provides a probe for internal use in medical operations, and particularly for use with laparoscopic surgery, that includes both a surgical device and an ultrasonic device with a field of imaging that either includes the surgical device or is immediately adjacent to the surgical device. In one embodiment, the surgical device is a tool designed for cutting and/or cauterizing tissue, such as, for example an electrocautery hook, a laser, or an ultrasonic cutter. Combining a surgical device in close proximity with an ultrasonic device on a probe is particularly advantageous when the surgical device is designed to cut and/or cauterize tissue, because the combination provides close control of the cutting operation to assure that only the intended tissue is actually cut and/or cauterized.

Figure 6:
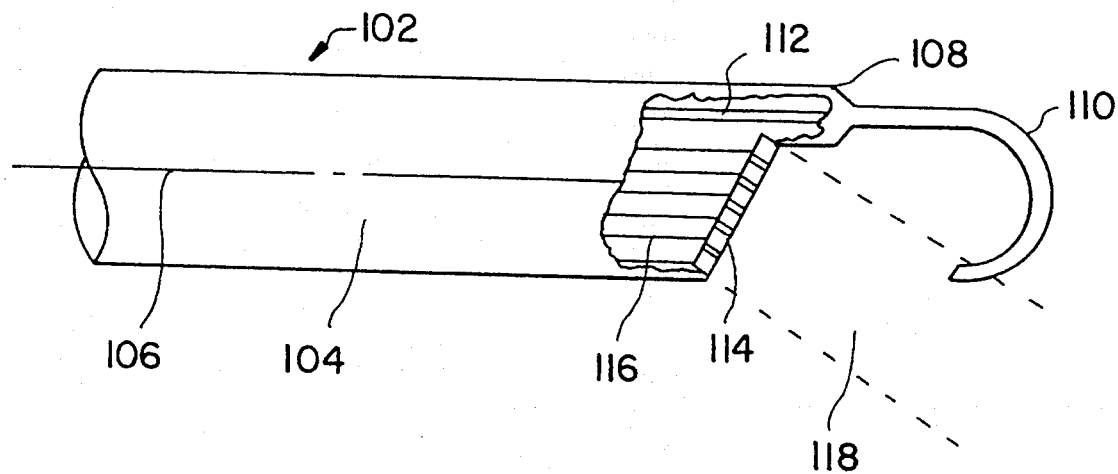
FIG. 6 shows a probe having an ultrasonic transducer array and an electrocautery hook located partially within the field of imaging of the array.

FIG. 6 shows one embodiment comprising an electrocautery hook. The probe 102 has a carrier 104 with a longitudinal axis 106 extending between a first terminal end 108 that enters into a patient's body and a second terminal end, not shown, that remains outside of the patient's body. Mounted at the first terminal end 108 is an electrocautery hook 110 that is connected to electrical wires 112 that supply electricity to the electrocautery hook to provide the required thermal energy for cutting and/or cauterizing tissue. Also mounted near the first terminal end is an array 114 having a plurality of ultrasonic transducer elements connected to electrical wires 116 that transmit electrical signals that are representative of an ultrasonic signal received by the array 114 that can be processed and displayed on a video monitor.

The ultrasonic transducer array 114 is mounted on the carrier in such a manner that the field of imaging includes the tip of the electrocautery hook 110. Therefore, a surgeon using such a probe would be able to simultaneously view the tissue to be cut and the tip of the electrocautery probe. The surgeon would, therefore, have a high degree of control in assuring that only the proper tissue is cut.

In some instances, it may be desirable to have improved side imaging capabilities. In such cases, it may be desirable to orient the field of imaging such that it does not actually include the surgical device, but is adjacent to the surgical device in such a manner that the surgeon can carefully control the location and operation of the surgical device to assure that the proper operation is performed. In some applications, it will be desirable to combine forward and side imaging capabilities using an ultrasonic transducer array combining both forward and side imaging features as previously discussed.

In yet a further aspect, the present invention provides an apparatus, such as a probe useful in laparoscopic surgery, and a method for establishing an ultrasonic circuit to facilitate ultrasonic imaging of body tissue of interest. The apparatus comprises a carrier, an ultrasonic device mounted on the carrier, and means for injecting an ultrasonically transmissive medium adjacent to the ultrasonic device.

Figure 7:
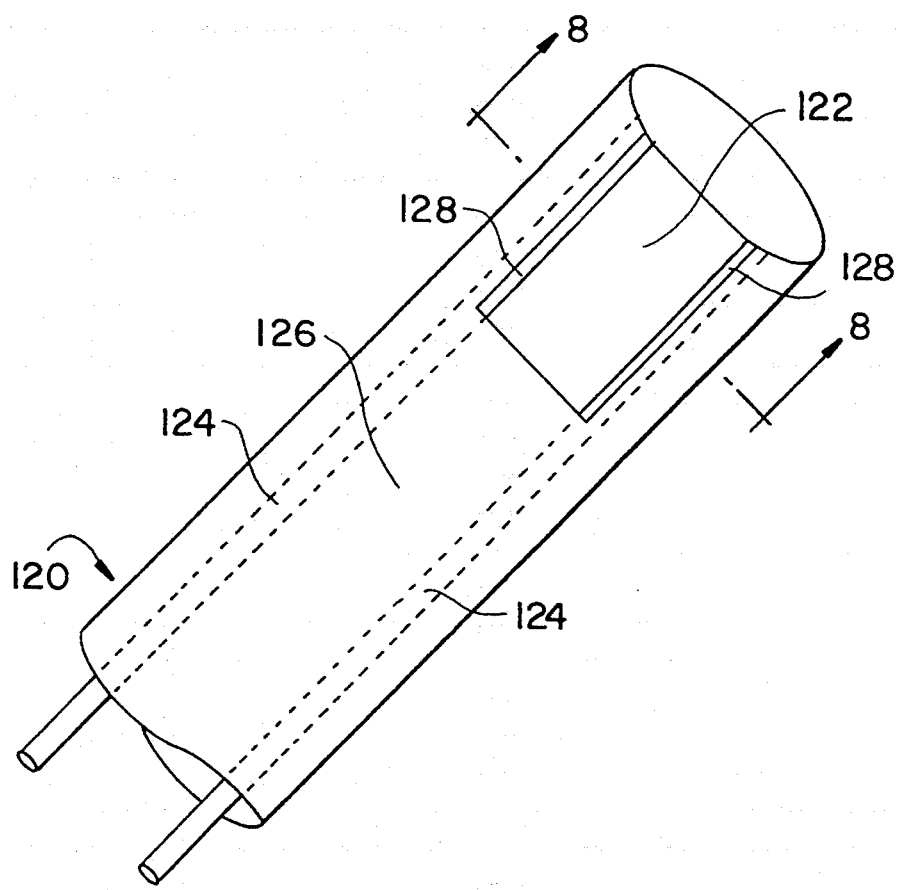
FIG. 7 shows a laparoscopic probe having an ultrasonic array and lumens for injecting transmissive fluid in the vicinity of an ultrasonic transducer array.
Figure 8:
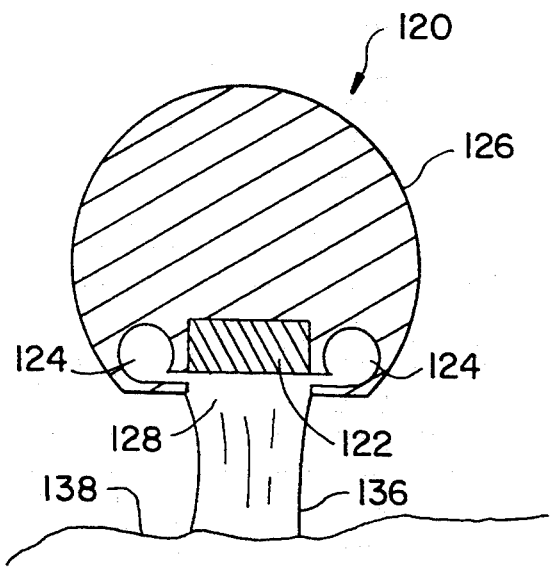
FIG. 8 shows a cross section of a probe having means for injecting transmissive fluid adjacent to an ultrasonic transducer array.

FIGS. 7 and 8 show a probe 120 having an array 122 of ultrasonic transducers and two lumens 124 passing through the carrier 126. The lumens 124 are used to transmit an ultrasonically transmissive medium 136 to openings 128 adjacent to the array 122 of transducer elements.

In the case of laparoscopic surgical operations, the probe 120 would be inserted into the patient's body and moved to a position as close as possible to tissue 138 of interest for the purpose of obtaining an ultrasonic image of that tissue. To establish, or to improve, ultrasonic contact between ultrasonic transducers of the array 122 and the tissue 138 of interest, an ultrasonically transmissive fluid is injected through the lumens 124 such that the ultrasonically transmissive fluid exits from openings 128 adjacent to the transducer array 122. Consequently, the ultrasonically transmissive fluid can establish an ultrasonic circuit between the array 122 and tissue 138 in the field of view of the array.

The transmissive medium can be any substance that is ultrasonically transmissive and capable of being injected through the lumens 124. Although water is ultrasonically transmissive, in one embodiment a higher viscosity fluid is used to reduce the tendency of the transmissive medium to disperse or flow away from the immediate vicinity of the transducer array 122. In one embodiment, a high viscosity fluid that has a viscosity of greater than about 20,000 cP, and preferably from about 20,000 cP to about 80,000 cP. One suitable high viscosity fluid include, for example, is sodium hyaluronate, having a viscosity of approximately 40,000 cP. Preferably, the high viscosity fluid, after being injected through the openings 128, adheres to the surface of the transducer 122 array and to the carrier 120 in the immediate vicinity, thereby forming an ultrasonically transmissive circuit between the transducer array 122 and the tissue 138 in the field of view of the transducer array 122 with little, if any, of the high viscosity fluid dispersing or flowing away from the area in the immediate vicinity of the transducer array and the tissue of interest. After imaging of tissue of interest is complete, the high viscosity fluid can be removed by applying suction to the lumens 124.

In one aspect, the present invention provides a disposable sheath for covering a probe, particularly for covering a laparoscopic probe having an ultrasonic device. The sheath covers the probe, thereby reducing or eliminating the need to sterilize the probe after use. The sheath covers the probe and extends from at least the terminal end of the probe that is inserted into the body cavity to a point on the probe that remains outside of the body cavity at all times. Preferably, the sheath covers the entire length of the probe.

Figure 9A:
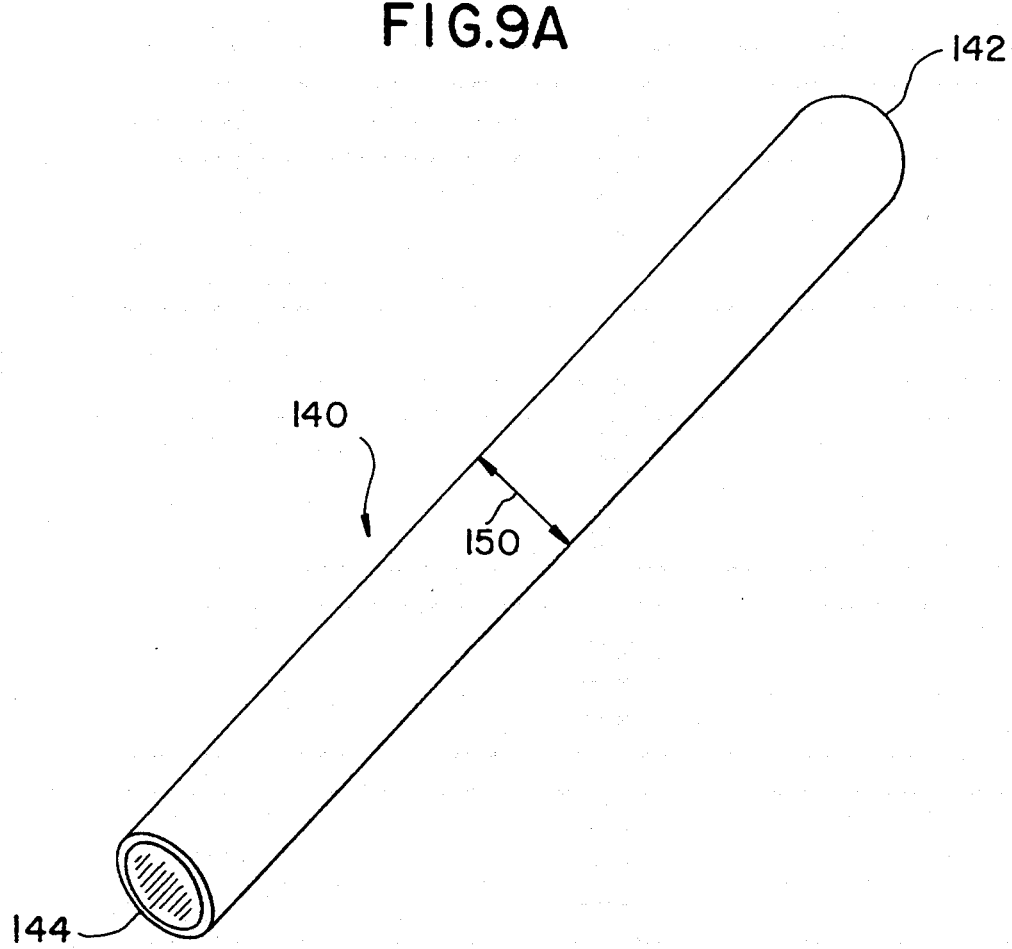
FIGS. 9A and 9B show a perspective view and a cross sectional view along the longitudinal axis of a first embodiment of a rigid sheath.
Figure 9B:
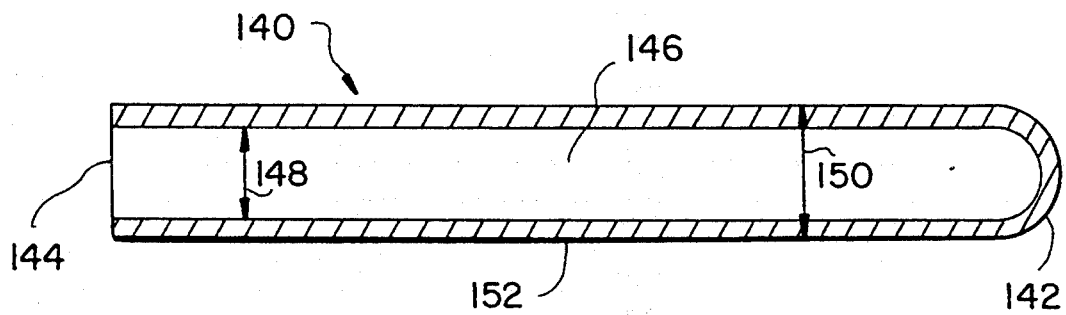

FIGS. 9A and 9B show a perspective view and a cross sectional view along the longitudinal axis of a rigid sheath 140 that is of a tubular shape designed to cover a generally tubular shaped laparoscopic probe having an ultrasonic device. The rigid sheath 140 has a first terminal end 142 that is inserted into a patient's body cavity along with the probe and a second terminal end 144 that remains outside of the body at all times. To cover a laparoscopic probe with the rigid sheath 140, the probe is inserted into the internal, hollow space 146 of the sheath. The rigid sheath 140 is preferably shaped to provide a close fit to the probe to be covered. Therefore, a tubular shaped sheath should be used to cover a tubular probe. Also, the fit between the laparoscopic probe and the rigid sheath should be of a close tolerance. Preferably, the maximum outside diameter of a tubular probe to be inserted into a tubular sheath should be not more than about 0.15 mm smaller than the internal diameter 148 of the rigid sheath 140.

The sheath 150, is preferably keyed with and latched to the probe inserted into the sheath in any fashion that prevents the sheath and the inserted probe from moving relative to one another during use of the probe. For example, the portion of probe, or the probe handle, which remain outside of the body during use could have a protrusion that corresponds to a keyed slot or recess in the sheath. The protrusion could also be spring actuated, for example, to latch into a recess in the sheath, thereby preventing the sheath and probe from moving relative to one another in either a rotational or translational direction.

The outer diameter 150 of the rigid sheath is smaller than the inside diameter of a cannula or surgical port. Preferably, the outer diameter 150 of the rigid sheath is not more than about 0.15 mm smaller than the diameter of the surgical port, being defined by the inner diameter of the smallest restriction through the cannula.

The rigid sheath 140 has a thin wall 152 that is preferably no greater than about 0.4 mm in thickness. The rigid sheath 140 can be made of any material, or combinations or composites of materials, that either alone or in combination with the tubular shape of the sheath provide the desired rigidity. By rigidity, it is meant that the structure of the sheath is such that material of the sheath will not bunch up, such as in folds, as would be experienced with a thin-walled, highly flexible sheath made of elastomeric-type material such as latex rubber, which can be sterilized. Rather, the rigid sheath 140, is a generally a self-supporting structure that resists such bunching of the material of the sheath. Therefore, the rigid sheath 140 reduces, or substantially eliminates, the binding problem associated with insertion and extraction of a probe covered by a sheath into and out of a patient's body through the cannula. Suitable materials for manufacture of the rigid sheath include, for example, metals, including steel, and relatively nonelastic polymeric compositions, such as those containing polycarbonates or polyethylenes. Polycarbonate-based compositions are particularly preferred because of the high biocompatibility and transparency of polycarbonates. Although transparency is not required, it is desirable so that the fit of the probe into the sheath can be observed at the time the probe is covered by the sheath.

Figure 10A:
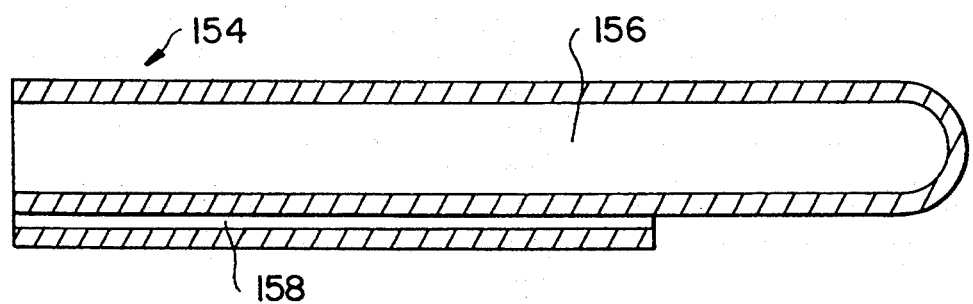
FIGS. 10A and 10B show a cross section along the longitudinal axis and a cross section perpendicular to the longitudinal axis of a second embodiment of a rigid sheath that also has a lumen that can be used for various purposes.
Figure 10B:
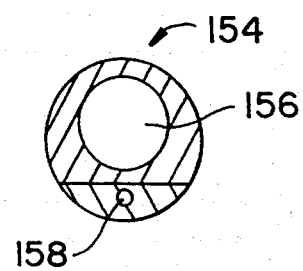

FIGS. 10A and 10B show a cross sectional view along the longitudinal axis and a cross sectional view perpendicular to the longitudinal axis of a second sheath 154 having a first interior, hollow space 156 in which a probe can be inserted prior to entry into a body cavity and second interior, hollow space 158 that is a lumen useful for transmitting fluids or surgical tools, such as a biopsy needle, to the area adjacent to the end of the probe, such as near the ultrasound imaging area of the probe. The sheath 154 is preferably a rigid sheath, as previously described.

Figure 11:
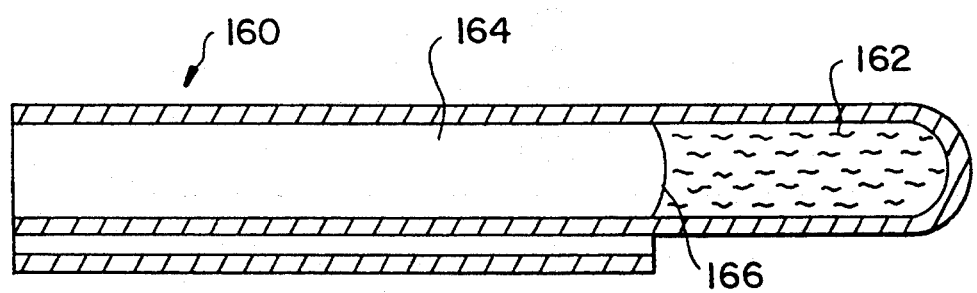
FIG. 11 shows another embodiment of the sheath having a chamber filled with transmissive medium and sealed with a breakable membrane.

FIG. 11 shows a third sheath 160 that is similar to the sheath previously described and shown in FIGS. 10A and 10B, except that the sheath 160 has a chamber 162 that contains an ultrasonically transmissive medium, such as a viscous fluid or deaerated water. The chamber is sealed and partitioned from other interior space of the sheath 164 by a thin membrane 166. The thin membrane 166 may be manufactured from any suitable material that is capable of sealing the chamber 162, but that can be pierced and ruptured by applying force to the membrane, such as by forcing a probe inserted into the sheath against and through the membrane 162. Suitable materials for manufacturing of the membrane 166 include, for example, polyethylene and polyvinyl chloride films.

Figure 12:
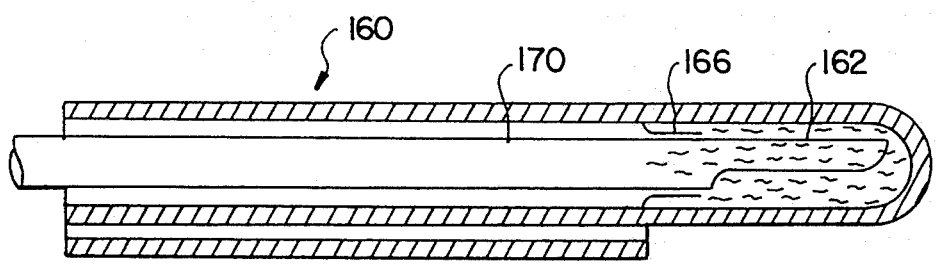
FIG. 12 shows the sheath of FIG. 11 in which the sealing membrane has been broken and a probe has been inserted into the chamber.

FIG. 12 shows the same sheath 160, but after the thin membrane 166 has been broken by insertion of an ultrasonic probe 170. Upon breaking the thin membrane 166, the probe is forced into the chamber 162 such that the transducer device of the probe is surrounded by ultrasonically transmissive medium that forms an ultrasonic circuit between the ultrasonic device and the sheath 160.

Figure 13:
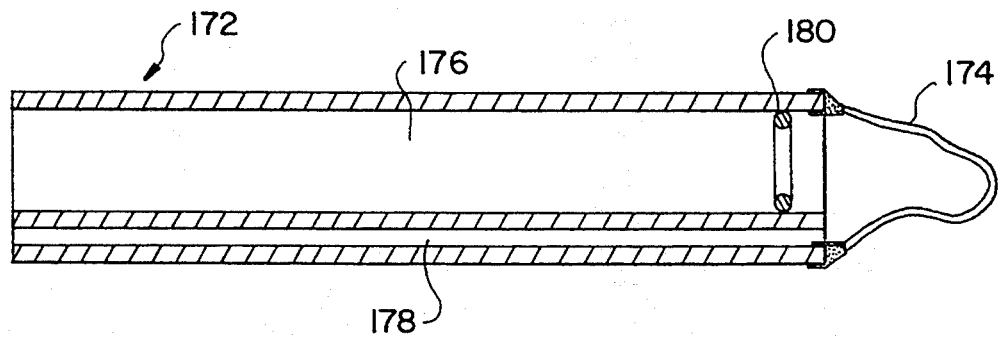
FIG. 13 shows another embodiment of the sheath having a balloon on the end that can be inflated with an ultrasonically transmissive medium through a lumen in the sheath.

FIG. 13 shows a fourth sheath 172 having attached at the terminal end, which enters into the body cavity, a balloon 174 that is made of an elastomeric-type material, such as latex rubber. The balloon 174 is in fluid communication with both the interior space 176 in which a probe can be inserted and a lumen 178 through which transmissive medium can be injected to inflate the balloon 174. The sheath 172 also has a sealing device 180 for sealing around the outer surface of a probe inserted through the sealing device 180. Such a sealing device could be, for example, an o-ring, chevron seals, or the like.

Figure 14:
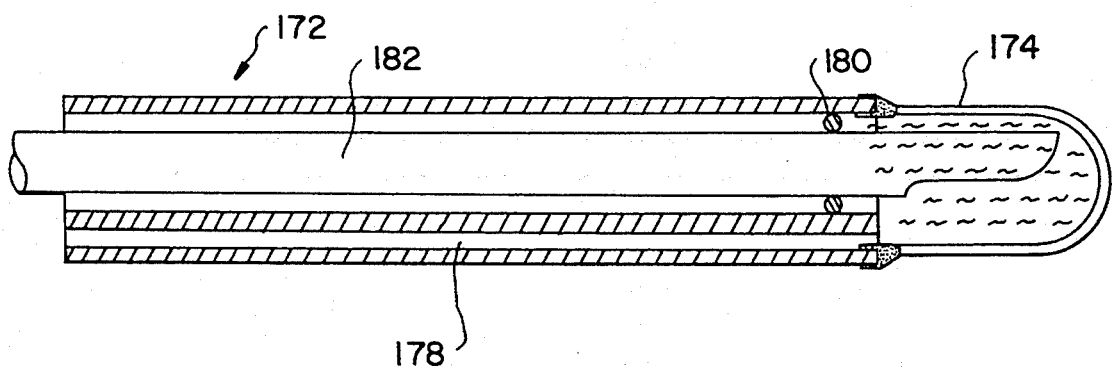
FIG. 14 shows the sheath of FIG. 13 with the balloon inflated with ultrasonically transmissive medium and in which an ultrasonic probe has been inserted.

FIG. 14 shows the same sheath 172 in which an ultrasonic probe 182 has been inserted. The probe 182, as shown, has been inserted through the sealing device 180 to form an annular seal about the outer surface of the probe 182. The balloon 174 has been inflated by the injection of ultrasonically transmissive medium through lumen 178, such that the ultrasonic device of probe 182 is surrounded by ultrasonically transmissive medium that establishes an ultrasonic circuit between the ultrasonic device and the balloon 174. By contacting the balloon with tissue of interest, an ultrasonic circuit can be established between the tissue and the ultrasonic probe. Also, the standoff distance provided between the inflated balloon and the ultrasonic device can significantly enhance ultrasound imaging.

Figure 15:
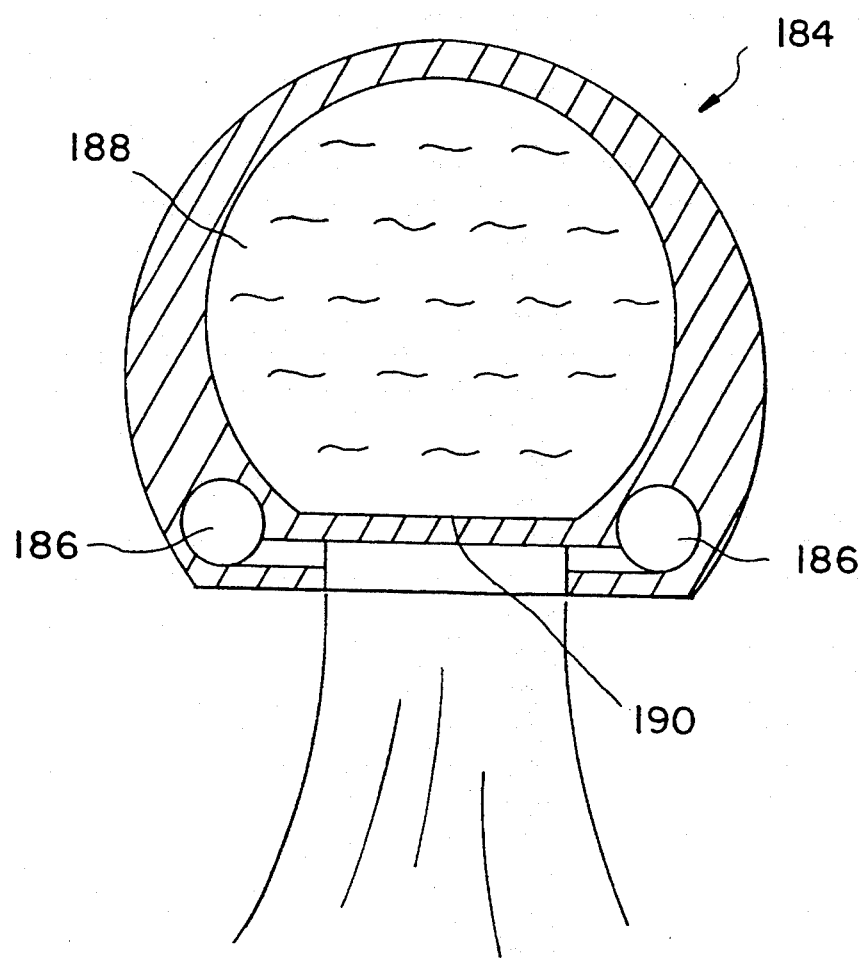
FIG. 15 shows a cross section of a sheath having lumens for placing transmissive medium in a area to be ultrasonically imaged.

FIG. 15 shows a cross section that is perpendicular to the longitudinal axis of a fifth sheath 184. The sheath 184 has two lumens 186 through which ultrasonic medium can be transmitted to and injected adjacent to the sheath, preferably at a distance along the longitudinal axis of the sheath corresponding to the position of an ultrasonic device on a probe inserted into the sheath. Preferably, ultrasonic medium injected through lumens 186 establishes an ultrasonic circuit between the sheath 184 and tissue of interest to be ultrasonically imaged. Preferably, a probe inserted into sheath 184 is positioned such that an ultrasonic device on the probe would be situated at a distance along the sheath's longitudinal axis that corresponds with the area where ultrasonic medium injected through lumens 186 would exit the sheath.

Suitable transmissive medium, would be any medium capable of transmitting ultrasound images, as previously discussed. In one case, the ultrasonically transmissive medium would be a high viscosity fluid that would adhere to the sheath following injection from lumens 186 in such a manner that the ultrasonically transmissive medium would not disperse or flow away from the sheath 184, and therefore, could be readily removed by suction through lumens 186 following ultrasound imaging.

Additionally, to establish an ultrasonic circuit between the ultrasonic device of a probe inserted into the sheath 184 and the sheath 184, an ultrasonically transmissive medium could be placed inside the interior space 188 of sheath 184.

The shape of sheath 184 is preferably designed so that the shape of the probe to be inserted into the sheath 184 and the shape of the sheath 184 are keyed so that the inserted probe and sheath can be rotated as a unit with the ultrasonic device of the probe correspondingly located to the position of the sheath 184 where ultrasonically transmissive medium may be injected through the lumens 186. For example, flat surface 190 of the sheath 184 could be keyed to a close tolerance probe design also containing a corresponding flat surface which contains an ultrasonic device.

Any aspect of the invention can be combined in any way with other aspects. Any of the features of probes shown in FIGS. 1A, 1B, 2A, 2B, 3, 6, 7 and 8 can be combined with image orientation and translation, as shown in FIG. 4, and/or any of the sheaths shown in FIGS. 9A, 9B, 10A, 10B, 11, 12, 13, 14 and 15, making appropriate modifications, as necessary. For example, a probe having a curved array portion and a linear array portion could be inserted into a rigid sheath having an electrocautery probe attached to the sheath with electrical wires to operate the sheath passing through a lumen attached to the sheath.

In a further aspect, the present invention provides a medical surgical apparatus that is useful in performing endosurgical operations. The apparatus is particularly useful for performing biopsies and other surgical operations.

Figure 16:
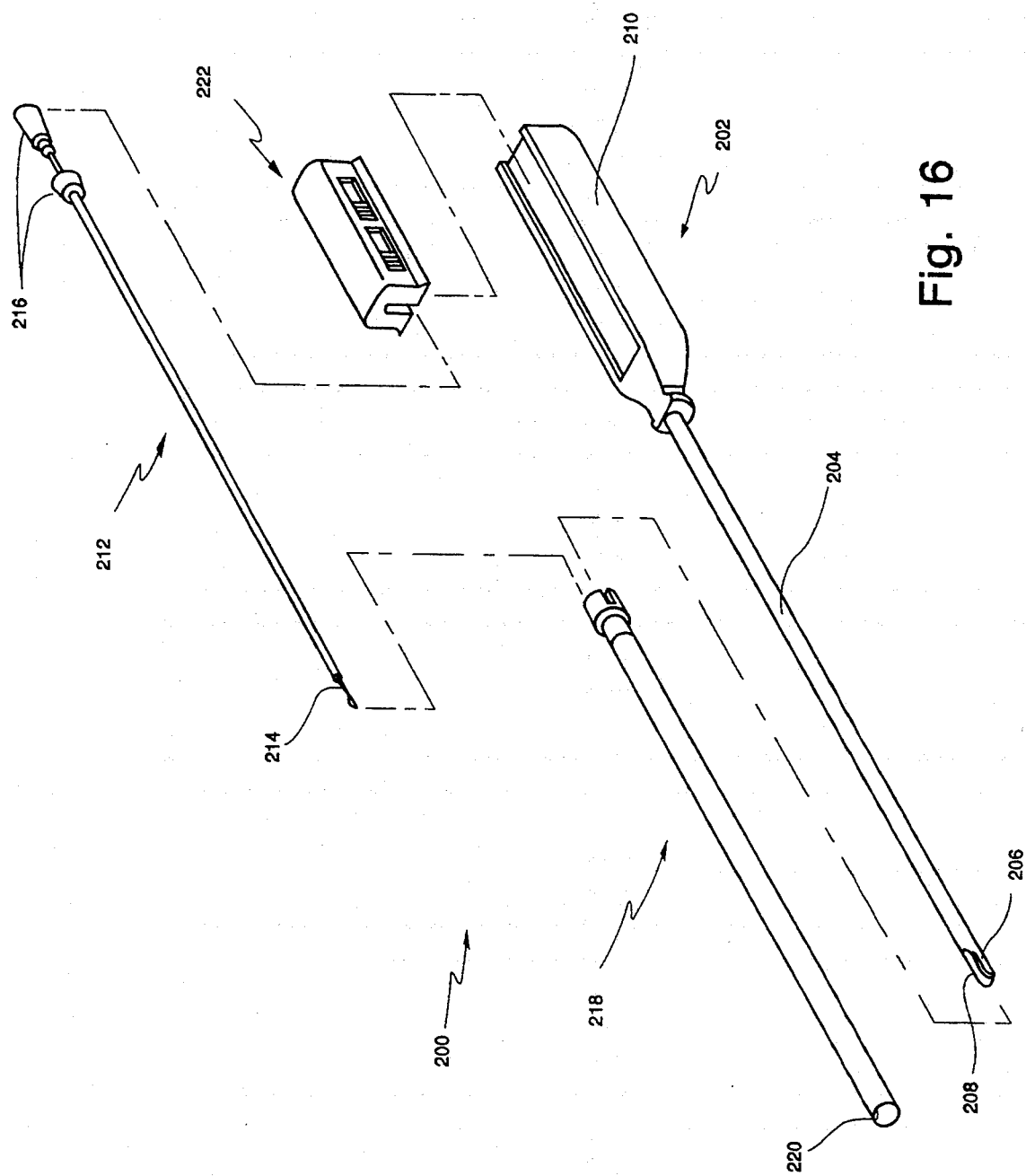
FIG. 16 is a perspective view in expanded form of a medical surgical apparatus including an ultrasonic imaging probe.

FIG. 16 shows generally a medical endosurgical apparatus 200, in expanded view, that has both ultrasonic imaging and biopsy capabilities. Generally, the apparatus 200 includes an ultrasonic imaging probe 202 for positioning an ultrasonic device adjacent to the tissue of interest so that an ultrasonic image of the tissue can be obtained. The ultrasonic imaging probe 202 includes a rod-shaped carrier 204 which has an insertion tip 206 with an ultrasonic device 208 for insertion into a patient's body during a medical endosurgical operation. The ultrasonic imaging probe 202 also has a handle 210 attached to the carrier 204 for use by a surgeon in grasping the probe and manipulating the location and positioning of the ultrasonic device 208 in a patient's body to ultrasonically image the tissue of interest.

A biopsy needle assembly 212 is used with the apparatus 200 for taking a biopsy sample of the tissue of interest. At one end of the biopsy needle assembly 212 are needle sampling tips 214 for insertion into the patient's body to obtain the tissue sample. At the other end are needle hubs 216 which remain outside of the patient's body for manipulation of the needle sampling tips 214.

The apparatus 200 further includes a rigid sheath 218, with a lumen 220, that can be placed over the carrier 204 of the ultrasonic imaging probe 202 for orienting the biopsy needle assembly 212 relative to the tip end 206 of the ultrasonic imaging probe 202 so that the needle sampling tips 214, when inserted through the lumen 220, are positioned within the field of view of the ultrasonic device 208. The rigid sheath 218 and the ultrasonic imaging probe 202 are engaged with one another in a keyed fashion to properly orient the lumen 220 of the rigid sheath 218 to the ultrasonic imaging probe 202.

Also included in the apparatus 200 is a biopsy actuator 222 for firing the biopsy needle assembly 212 to take a biopsy sample. The biopsy actuator 222 may be mounted on probe handle 210 so that a surgeon may grasp and manipulate both the ultrasonic imaging probe 202 and the biopsy actuator 222 with a single hand. The needle hubs 216 are disposed in biopsy actuator 222 and, when biopsy actuator 222 is fired, the needle sampling tips 214 are correspondingly moved to take a biopsy sample.

FIGS. 17–20 are used to further describe one embodiment of the ultrasonic imaging probe 202. Referring to FIG. 17, the ultrasonic imaging probe 202 has the rod-shaped carrier 204 for insertion into a patient's body. Mounted adjacent the insertion tip 206 of the carrier 204 is the ultrasonic device 208 for receiving an ultrasonic signal from the tissue underlying the ultrasonic device 208 that is representative thereof and for generating an electrical signal that is representative of the received ultrasonic signal. The electrical signal is used to prepare an ultrasonic image of the underlying tissue within the body cavity. Ultrasonic device 208 may also transmit ultrasonic signals which, when reflected off of tissue within the field of view of the ultrasonic device 208, provide ultrasonic signals for receipt by ultrasonic device 208. The ultrasonic device 208 preferably comprises the capability to ultrasonically image tissue in front of the carrier 204 and more preferably comprises an array of ultrasonic transducers arranged in a linear array portion 228 for imaging tissue to the side of the carrier 204 and a curved array portion 230 for imaging tissue in front of the carrier 204.

The carrier 204 is particularly suited for endosurgical procedures. The carrier 204 has a substantially circular cross-section over much of its length to facilitate insertion through the substantially circular surgical port, which is generally established by a trocar or similar device. The substantially uniform circular cross-section also provides a good sealing surface to which an annular seal may be established between the wall of the surgical port and the outside surface of the carrier. Such a seal can be effected while the carrier 204 is stationary and while the carrier is sliding through the surgical port. The carrier 204 deviates from the substantially circular cross-section shape only near the insertion tip 206 where the ultrasonic device 208 is mounted in a position that curves toward the insertion tip 206. All of the carrier 204, however, including the ultrasonic device 208, lies within the areal boundary of the substantially uniform circular cross-section to permit easy insertion and removal of all of the carrier 204 through the surgical port. The outside diameter of the carrier 204 is also typically smaller than about 12 millimeters, and is preferably 10 mm or smaller, for easy insertion into the small diameter surgical ports used during endosurgery.

The carrier 204 is attached to probe handle 210 which may be grasped by a surgeon to manipulate the position of ultrasonic device 208 in a patient's body. As shown in FIG. 18, probe handle 210 has a generally rounded side 226 on the bottom providing a comfortable contour for grasping by a surgeon and a flat side 236 on top for mounting of the biopsy actuator 222 and for orienting probe handle 210 to the rigid sheath 218.

Grooved into the flat side 236 of the probe handle 210 is a slot 232 for receiving a corresponding rail on a biopsy actuator 222 to mount the biopsy actuator 222 on the probe handle 210 during a biopsy procedure. As shown in FIG. 17, ultrasonic device 208 is located on the side of the carrier 204 that corresponds with flat side 236 of probe handle 210 so that the portion of the biopsy needle assembly 212 that projects from the mounted biopsy actuator 222 is oriented with ultrasonic device 208. The portion of the biopsy needle assembly 212 that projects from the mounted biopsy actuator 222 can then be positioned within the field of view of ultrasonic device 208 to facilitate the taking of a biopsy sample. Slot 232 extends longitudinally along flat surface 236 of probe handle 210, thereby permitting a biopsy actuator 222 to be slidably mounted such that the biopsy actuator 222 may be translated longitudinally on probe handle 210 for positioning the biopsy actuator 222 relative to the ultrasonic imaging probe 202.

On the end of the probe handle 210 that is adjacent the carrier 204 is a keyed engagement structure 233 for engaging and orienting the rigid sheath 218, which is used with the ultrasonic imaging probe 202 during a biopsy procedure. The keyed engagement structure 233 of the ultrasonic imaging probe 202 and the cooperating structure of the rigid sheath 218 are keyed to one another to orient to the rigid sheath and the ultrasonic imaging probe 202 so that the lumen 220 extending through the rigid sheath 218 is aligned with flat side 236 of probe handle 210 to guide the portion of the biopsy needle assembly 212 exiting the mounted biopsy actuator 222 into the field of view of the ultrasonic device 208 adjacent insertion tip 206. FIG. 19, a cross-sectional view of probe handle 210 at the keyed engagement structure 233, shows a rounded raised lip 234 on the bottom of the handle 210 and a flat side 236 on the top of the handle 210. The raised lip 234 provides an engaging surface for a cooperating rigid sheath engagement structure on the rigid sheath 218 and the raised lip 234 and flat side 236, together, form a keyed engagement shape that, in cooperation with the rigid sheath 218 engagement structure, orients the rigid sheath 218 to the probe 210.

Figure 20:
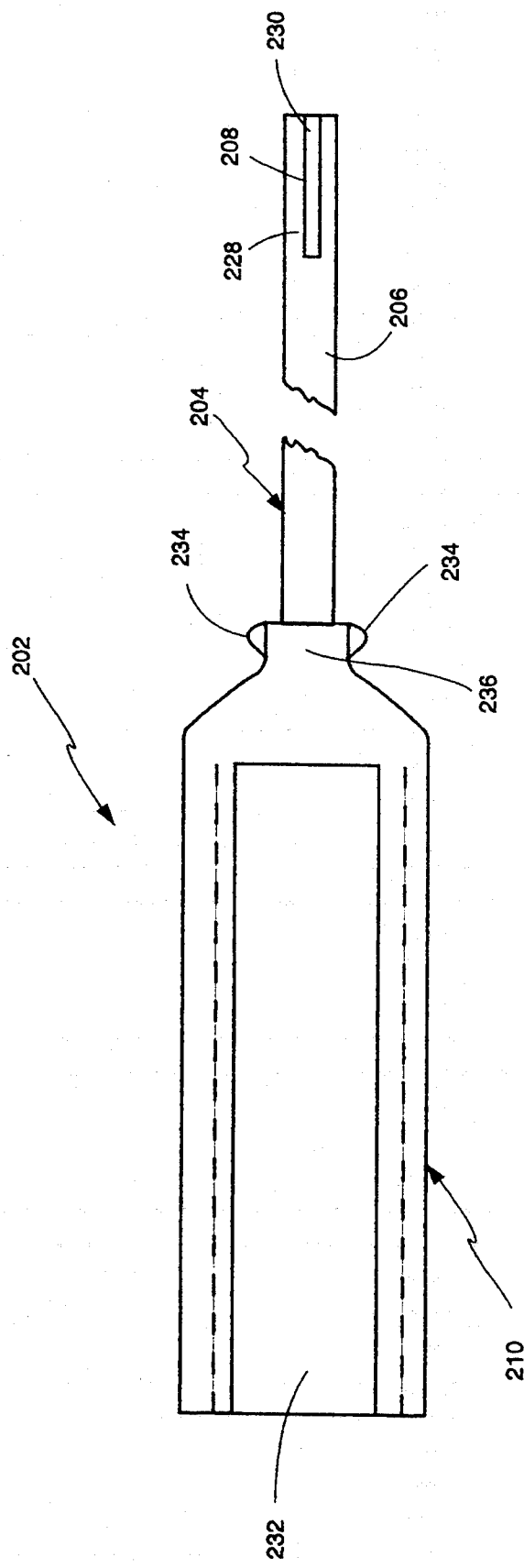
FIG. 20 is a top view of one embodiment of an ultrasonic imaging probe.

Ultrasonic imaging probe 202 is further shown in a top view in FIG. 20 showing probe handle 210 with slot 232 for mounting of the biopsy actuator 222 and with raised lip 234 and flat side 236 for engaging and keying with the rigid sheath 218 that is placed over the carrier 204 during biopsy procedures.

Figure 21:
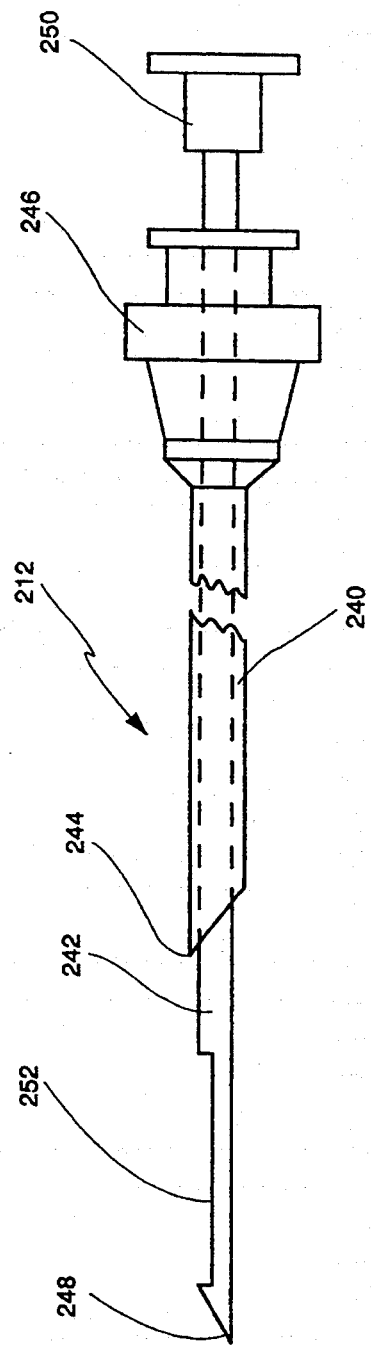
FIG. 21 is a side view of a biopsy needle assembly.

FIG. 21 shows a typical biopsy needle assembly 212 which can be used with the apparatus 200 to take a biopsy sample. The biopsy needle assembly 212 comprises two needles, a hollow needle 240, called a cannula, and a solid needle 242, called a stylet, which is disposed inside of the cannula. The cannula 240 has a cutting tip 244 which is inserted into the patient's body during the taking of a biopsy sample and a needle hub 246, which remains outside of the patient's body, for manipulating cutting tip 244. The stylet 242 has a piercing tip 248 for piercing tissue inside of a patient's body during the taking of a biopsy sample and a needle hub 250, which remains outside of the patient's body, for manipulating the piercing tip. The stylet 242 also has a tissue sampling notch 252 in which a biopsy tissue sample can be collected.

In taking a biopsy sample with the biopsy needle assembly 212, the piercing tip 248 of the stylet 242 is initially in a retracted position substantially within the hollow interior of the cannula 240. The needle hub 250 of the stylet 242 is then moved relative to the needle hub 246 of the cannula 240 such that piercing tip 248 of the stylet 242 exits from the cannula 240 to pierce the tissue of interest with piercing tip 248 and to fill tissue sampling notch 252 with the tissue to be sampled. The needle hub 246 of the cannula 240 is then moved relative to needle hub 250 of the stylet 242 so as to move the cutting tip 244 of the cannula 240 down over the tissue sample filling tissue sampling notch 252 of the stylet 242, thereby severing the tissue sample from the patient's body and holding the severed sample in tissue sampling notch 252 which ends up substantially completely within the cannula 240. The biopsy needle assembly 212 can then be removed from the patient's body and the collected tissue sample can be recovered for analysis.

The apparatus 200 also includes a rigid sheath that can be placed over an ultrasonic imaging probe to facilitate the taking of biopsy samples by facilitating positioning of the biopsy needle assembly 212 in the field of view of an ultrasonic device 208 on the ultrasonic imaging probe 202.

FIGS. 22–26 show one embodiment of the rigid sheath 218 having a hollow interior in which the ultrasonic imaging probe 202 can be disposed. Referring first to FIG. 22, the rigid sheath 218 includes a first portion 256 for fitting over the rod-shaped carrier 204 of ultrasonic imaging probe 202 and for inserting, with the rod-shaped carrier 204 into a patient's body. The rigid sheath 218 also has a second portion 258 for connecting the rigid sheath 218 to an ultrasonic imaging probe 202 and for orienting the rigid sheath 218 to the ultrasonic imaging probe 202 such that the portion of the biopsy needle assembly 212 passing through the lumen 220 can be positioned in the field of view of an ultrasonic device 208. FIG. 23A is a cross-section of first portion 256 showing the lumen 220 attached to the inside wall of the rigid sheath 218. FIG. 23B shows a possible alternative cross-sectional view for the rigid sheath 218 in which the lumen 220 is placed within the wall of the rigid sheath 218, such as could result by co-extruding the lumen 220 with the interior hollow portion of the rigid sheath 218 using an extruded plastic material of construction.

The rigid sheath 218 has a substantially circular cross-sectional shape over the length of the first portion 256 to facilitate easy insertion, removal, and sealing relative to a surgical port in similar manner as previously discussed with the shape of the carrier 204 of the ultrasonic imaging probe 202. The lumen 220 is substantially entirely within the substantially circular cross-section so as not to interfere with insertion, removal and sealing relative to the surgical port. Typically, the first portion of rigid sheath 218 has an outside diameter of no more than about 2 millimeters larger than the diameter of carrier 204. Therefore, the first portion 256 of rigid sheath 218 might have an outside diameter of 12 millimeters to correspond to a carrier 204 of 10 millimeters in diameter.

Referring again to FIG. 22, the second portion 258 has a rigid sheath keyed engagement structure 259 for engaging the corresponding engagement structure 233 of the ultrasonic imaging probe 202 and orienting the rigid sheath 218 relative to the ultrasonic imaging probe 202. The keyed engagement structure 259 includes a connecting clip 260 for snapping over and engaging the raised lip 234 on the ultrasonic imaging probe 202. The sectional view in FIG. 24 shows the hollow lip shape of the connecting clip 260 for engaging the raised lip 234 on the ultrasonic imaging probe 202.

As shown in FIG. 22, the keyed engagement structure 259 also has an orientation guide 262 which, together with connecting clip 260, forms a keyed shape for orienting the rigid sheath to the ultrasonic imaging probe 202. Specifically, the connecting clip 260 and the orientation guide 262 of the rigid sheath 218 cooperate with the raised lip 234 and flat side 236, respectively, of the probe handle 210 to orient the rigid sheath 218 to the probe handle 210. When the rigid sheath 218 is connected to the ultrasonic imaging probe 202, the rigid sheath 218 is oriented relative to the ultrasonic imaging probe 202 by the keyed engagement shape so that the biopsy needle assembly 212 passing through the lumen 220 will exit the first portion 256 of the rigid sheath 218 in the field of view of the ultrasonic device 208 on the ultrasonic imaging probe 210. The end view of the rigid sheath 218 in FIG. 25 further shows connecting clip 260 and orientation guide 262 having substantially flat orientation surface 264.

Orientation guide 262, as shown in FIG. 25, also has a needle guide 266 for guiding a biopsy needle assembly to the entry port of the lumen 220 for easy insertion of the biopsy needle assembly 212 into the lumen 220. As shown in the sectional view in FIG. 26 of orientation guide 262, the needle guide 266 is in the form of a flared recess, with the narrow end of the flare being positioned adjacent the entry port of the lumen 220 to guide the biopsy needle assembly 212 into the lumen 220.

Figure 27:
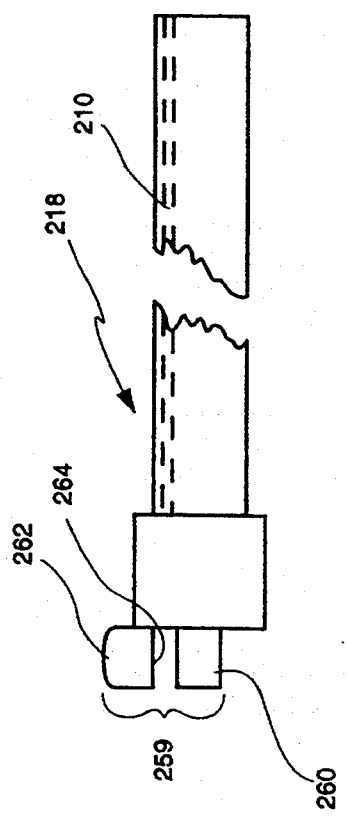
FIG. 27 is a side view of one embodiment of a rigid sheath having two connecting clips for engaging an ultrasonic imaging probe.
Figure 28:
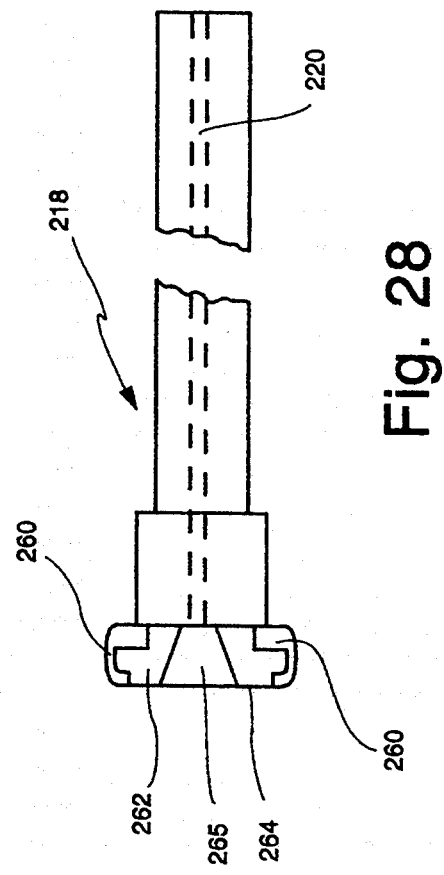
FIG. 28 is a bottom view of one embodiment of a rigid sheath having two connecting clips for engaging an ultrasonic imaging probe.

FIGS. 27 and 28 show another embodiment of the rigid sheath 218 with an alternative design for connecting and orienting the rigid sheath 218 to an ultrasonic imaging probe 202. The rigid sheath 218, as shown in FIGS. 27 and 28, is substantially the same as shown in FIGS. 22–26, except as noted. In particular, FIGS. 27 and 28 show the rigid sheath 218 with keyed engagement structure 259 including a pair of opposing connecting clips 260 having a hook-like shape on one side for engaging the raised lip 234 on an ultrasonic imaging probe 202. Orientation guide 262 has a substantially flat orientation surface 264, which in combination with connecting clip 260, key the rigid sheath 218 to the flat side 236 and raised lip 234 of the ultrasonic imaging probe 202. The needle guide 266 in the form of a flared recess helps guide a biopsy needle assembly for easy insertion into the lumen 220.

The rigid sheath 218 has been described for use with the ultrasonic imaging probe 202 for performing a biopsy. The utility of rigid sheath 218 is not limited, however, to use with the biopsy actuator 222. For example, the ultrasonic imaging probe 202 and the rigid sheath 218 can be used without the biopsy actuator 222 to perform many endosurgical procedures. For example, a biopsy can be performed manually, without the aid of the automatic actuation provided by biopsy actuator 222, using the probe 202 and the rigid sheath 218.

The rigid sheath 218 can also be used to perform endosurgical procedures other than biopsies in which it may be convenient to pass endosurgical tools through lumen 220 for positioning within the field of view of the ultrasonic device 208. Endosurgical tools, including a biopsy needle assembly, which can be passed through the lumen 220 are generally referred to as insertion devices. The rigid sheath 218 can be used with many different types of insertion devices, whether manually or automatically actuated. For example, a hollow needle can be passed through lumen 220 and positioned at a location of interest inside of a patient's body using the ultrasonic imaging capability of the ultrasonic device 208 of the ultrasonic imaging probe 202. A guide wire can then be inserted through the hollow needle for use in guiding subsequent insertion devices, such as a cryoprobe or a catheter, to the location of interest inside of the patient's body cavity.

The rigid sheath of the present invention can be manufactured from any material or materials having sufficient structural rigidity to prevent significant flexure of the rigid sheath relative to an ultrasonic imaging probe disposed therein. Any materials are acceptable that are capable of being shaped into the form of the rigid sheath of the present invention such that the rigid sheath is a self-supporting structure. As used herein, self-supporting structure refers to a rigid sheath structure that maintains substantially the same shape with an ultrasonic imaging probe inserted therein as the shape of the rigid sheath when it is free-standing, i.e., with no ultrasonic imaging probe disposed therein. Examples of suitable materials include thermosetting compositions such as epoxy glass composites and thermoplastics such as polyesters, polycarbonates and rigidized PVC. Although the rigid sheath of the present invention may be sterilized for reuse, an advantage of the rigid sheath is that it can be made relatively inexpensively and can, therefore, be economically disposed of after a single use, thereby avoiding the cost and complexity of sterilization for reuse.

The apparatus 200, as shown in FIG. 1, also includes the biopsy actuator 222 that can be mounted on the handle 210 of an ultrasonic imaging probe 202 to assist in accurately taking a biopsy sample with a biopsy needle assembly that is disposed in the biopsy actuator 222. More specifically, the biopsy actuator 222 is designed to be mounted on the handle 210 of the ultrasonic imaging probe 202 to facilitate grasping and manipulation with one hand of both the biopsy actuator 222 and the handle 210 of the ultrasonic imaging probe 202.

Referring to FIGS. 29-31, the biopsy actuator 222 includes a housing 272 for containing the working mechanisms of the biopsy actuator 222 and for providing a contoured surface for a surgeon to comfortably grasp. On one side of housing 272 is a rail 274 which mates with the corresponding slot 232 on the handle 210 of an ultrasonic imaging probe 202 to slidably mount the biopsy actuator 222 on the probe handle 210. Slidable mounting of the biopsy actuator 222 on a probe handle 210 permits the surgeon to translate the biopsy actuator 222 longitudinally along the probe handle 210, thereby allowing positioning of the biopsy actuator 222 relative to the probe handle 210 and, hence, also allowing the portion of the biopsy needle assembly 212 that projects from the biopsy actuator 222 to be positioned relative to an ultrasonic device 208 adjacent the insertion tip of the ultrasonic imaging probe 202.

As shown in FIGS. 30 and 31, housing 272 has a generally rounded shape on the side opposite rail 274. The rounded shape provides good contour for grasping of the biopsy actuator 222 and the probe handle 210 on which the biopsy actuator 222 is mounted, which has the rounded side 226 located opposite to the side on which the biopsy actuator 222 is mounted.

Figure 32:
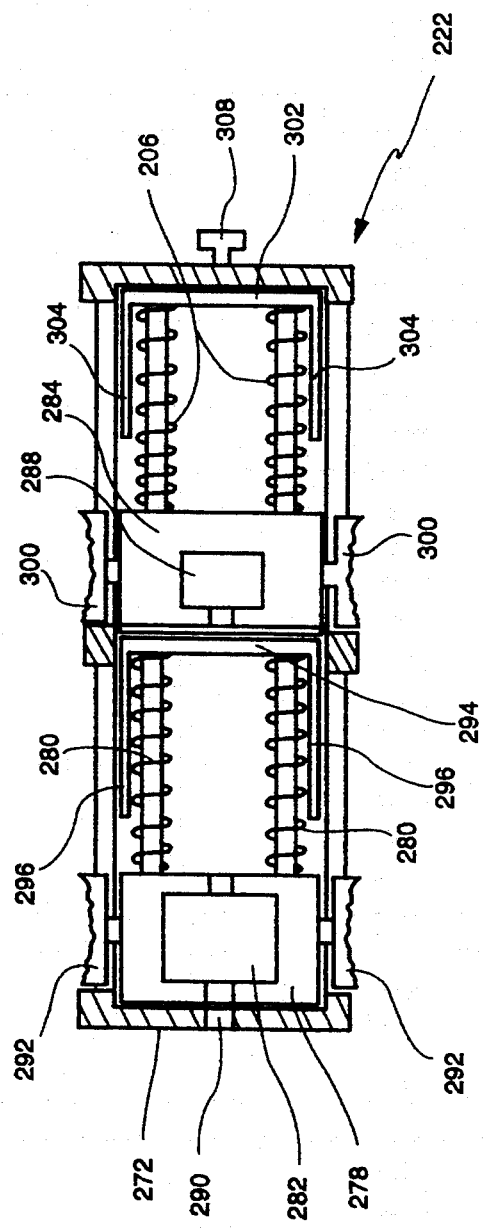
FIG. 32 is a cut-away of one embodiment of a biopsy actuator.

FIG. 32 is a cut-away of the biopsy actuator 222 showing the breach mechanism for firing the biopsy needle assembly 212 to take a biopsy sample. The breach mechanism includes a cannula slide 278 for propelling the cannula 240 of the biopsy needle assembly 212 during the taking of a biopsy sample. The cannula slide 278 is shown biased in a forward position by springs 280. The cannula slide 278 has a recess area 282 for receiving the needle hub 246 of the cannula 240. The breach mechanism also includes a stylet slide 284 for propelling the stylet 242 during the taking of a biopsy. The stylet slide 284 is shown biased in a forward position by springs 286. The stylet slide 284 has a recess area 288 for receiving the needle hub 250 of the stylet 242. An opening 290 through the wall of housing 272 is provided through which the cannula 240 and the stylet 242 of the biopsy needle assembly 212 can extend from the needle hubs 246 and 250 which are held, respectively, in cannula slide 278 and the stylet slide 284.

Figure 33:
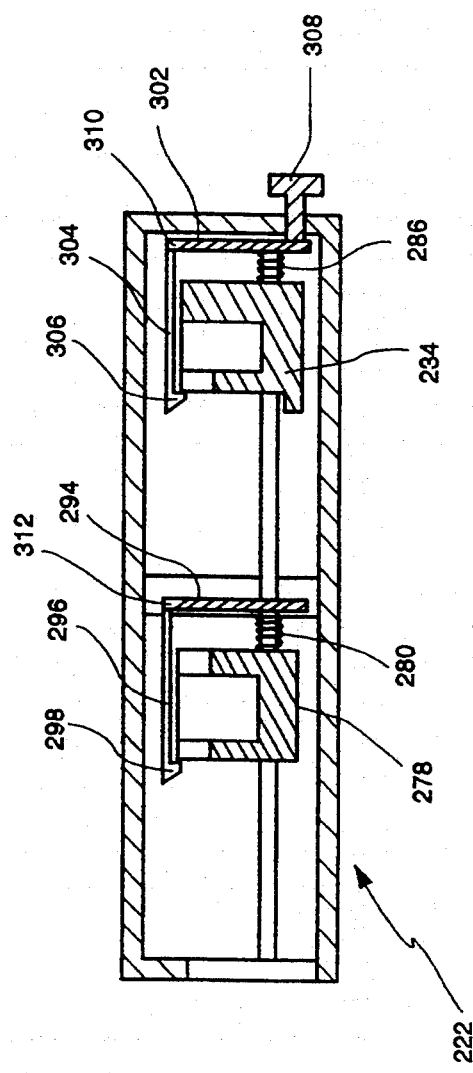
FIG. 33 is a sectional view showing one embodiment of a biopsy actuator in a cocked position.

Biopsy actuator 222 also includes a cocking mechanism for retracting and retaining the cannula slide 278 against the force of compressed springs 280 and for retracting and retaining the stylet slide 284 against the force of compressed springs 286. The cocking mechanism includes a pair of cannula cocking grips 292 (shown in FIGS. 29, 32 and 34) for use in retracting the cannula slide 278 towards the back of biopsy actuator 222 against the bias of springs 280 to cock the cannula slide 278. The cannula cocking grips 292 are located on opposite sides of housing 272 from each other to facilitate easy gripping of the cannula cocking grips 292, such that one of the cannula cocking grips 292 can be gripped with a thumb and the other of the cannula cocking grips 292 can be gripped with an opposing finger of the same hand. The cocking mechanism also includes a cannula sear 294 pivotally attached to housing 272 and having two cannula retaining arms 296 for retaining the cannula slide 278 in a cocked position against compressed springs 280. Referring to FIG. 33, showing a sectional view of biopsy actuator 222 in a cocked position, the cannula retaining arms 296 have a hooked end 298 which hooks over the cannula slide 278 to retain the cannula slide 278 in a cocked position.

Figure 34:
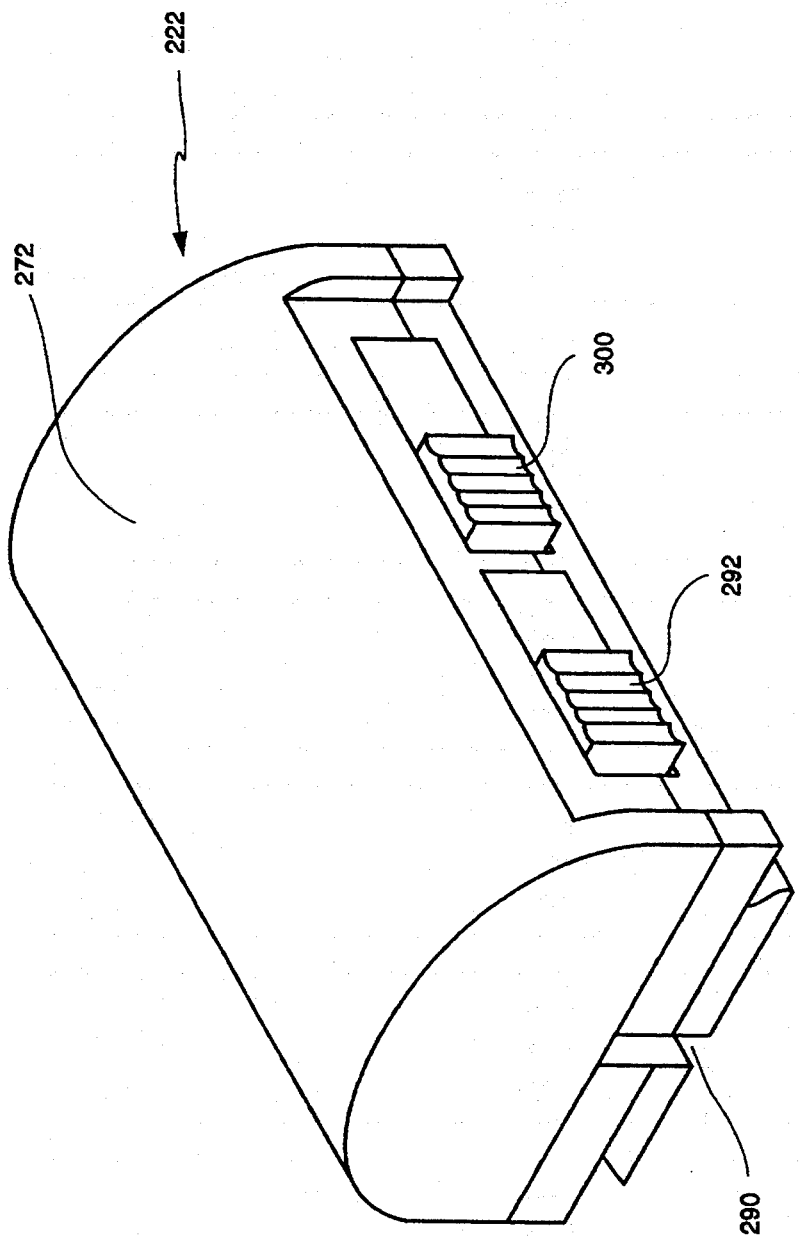
FIG. 34 is a perspective view of one embodiment of a biopsy actuator.

The cocking mechanism also includes a pair of stylet cocking grips 300 (as shown in FIGS. 29, 32 and 34) for retracting the stylet slide 284 towards the back of biopsy actuator 222 against the bias of springs 286 to cock the stylet slide 284. The stylet cocking grips 300 are located on opposite sides of housing 272, to facilitate easy griping for cocking, in the same manner as previously described for the cannula cocking grips 292. The cocking mechanism also includes a stylet sear 302 pivotally attached to housing 222 and having two stylet retaining arms 304 for retaining the stylet slide 284 in a cocked position against compressed springs 286. As shown in FIG. 33, the stylet retaining arms 304 have a hooked end 306 which hooks over the stylet slide 284 to retain the stylet slide 284 in a cocked position.

Biopsy actuator 222 also includes a firing mechanism for firing the biopsy actuator to release the cannula slide 278 and the stylet slide 284 from cocked positions, thereby propelling a stylet 242 and the cannula 240 of the biopsy needle assembly 212 to take a biopsy sample of tissue in a patient's body. Referring to FIGS. 32 and 33, the firing mechanism includes a firing button 308 on the back of the biopsy actuator 222. As shown in FIG. 33, firing button 308 contacts the stylet sear 302 and when pushed, pivots the stylet sear 302 about pin 310, lifting the hooked end 306 of the sear 302 to release the stylet slide 284 from a cocked position and allow spring 286 to expand, thereby propelling the stylet slide 284 to a forward position. The stylet slide 284 eventually strikes the cannula sear 294, causing the cannula sear 294 to pivot about pin 312 and lift hooked end 298, thereby releasing the cannula slide 278 from a cocked position and allowing spring 280 to expand, thereby propelling the cannula slide 278 towards the front of the biopsy actuator 222 in phased sequence to the propulsion of the cannula slide 284.

Figure 36:
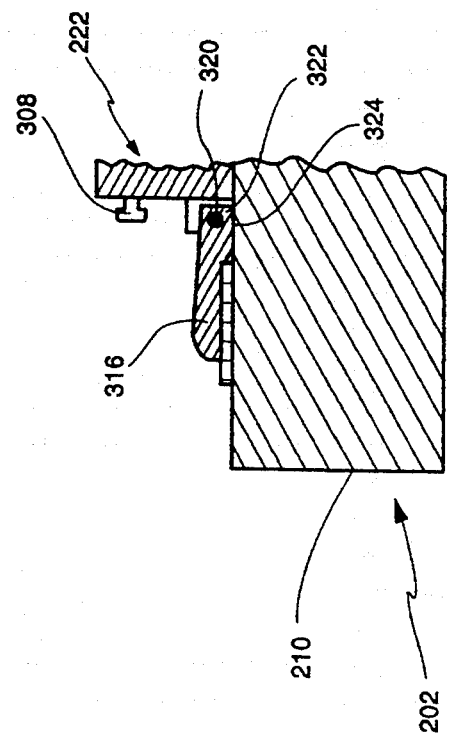
FIG. 36 is a partial sectional view of one embodiment of a biopsy actuator device mounted on an ultrasonic imaging probe handle having a safety device.
Figure 35:
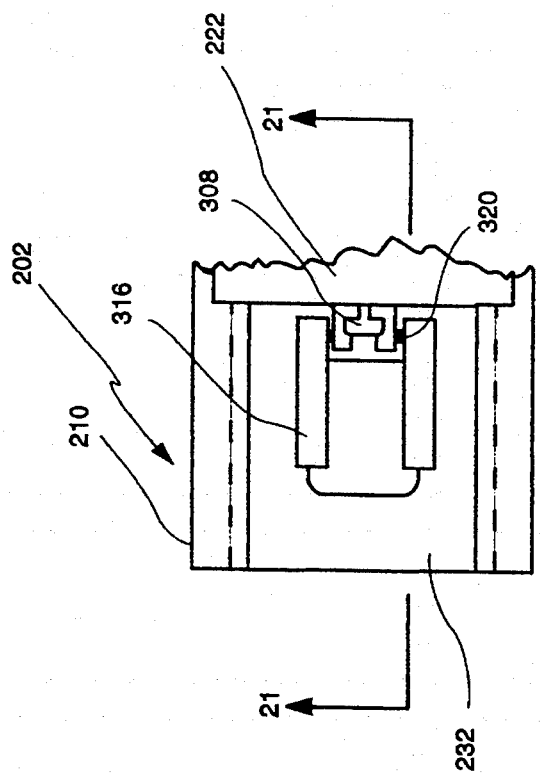
FIG. 35 is a partial top view of one embodiment of a biopsy actuator mounted on an ultrasonic imaging probe handle and having a safety device.

Biopsy actuator 222 also includes a safety locking mechanism for preventing the accidental firing of the biopsy actuator 222 and locking the biopsy actuator 222 in place on the handle 210. Referring to FIGS. 29 and 31, the safety mechanism includes a safety cover 316 which normally covers firing button 308. Safety cover 316 is pivotally mounted to housing 272 and is biased in a closed position by spring 318. Referring to FIGS. 35 and 36, safety cover 316 can be opened to expose firing button 308 by pivoting safety cover 316 about pin 320.

FIGS. 35 and 36 show partial views of the biopsy actuator 222 mounted on a probe handle 210 of an ultrasonic imaging probe 202 that demonstrate the locking aspect of the mechanism. An additional feature of safety cover 316 is that it has a squared edge 322 which, upon pivoting of safety cover 316 to an "off-safety" position in which the firing button 308 is exposed, wedges against the surface 324 of the probe handle 210 with sufficient force to lock the biopsy actuator 222 in a fixed position relative to the probe handle 210. As a consequence, the portion of the biopsy needle assembly 212 exiting the biopsy actuator 222 would also be locked in position relative to the ultrasonic device 208 on the insertion tip 206 of the ultrasonic imaging probe 202 to facilitate accurately taking a biopsy sample of the desired tissue.

It should be recognized that the locking mechanism could be any mechanism capable of freezing the relative positions of the ultrasonic imaging probe 202 and the biopsy actuator 222. Such mechanisms include a breaking structure, a detent structure and others.

FIG. 34 shows a perspective view of assembled biopsy actuator 222 with the housing 272 having a contoured shaped for easy grasping in combination with the rounded side 226 of the probe handle 210 and with the cannula cocking grips 292 and the stylet cocking grips 300 positioned on the side of the biopsy actuator 222 for easy cocking by a surgeon. When mounted on the probe handle 210 of the ultrasonic imaging probe 202, the opening 290, through which the biopsy needle assembly 212 would extend during use, is oriented to position the lumen 220 in the rigid sheath 218 for receiving and guiding a portion of the biopsy needle assembly 212 to within the field of view of the ultrasonic device 208 on the insertion tip 206 of the ultrasonic imaging probe 202 over which the rigid sheath 218 is disposed.

Figure 37:
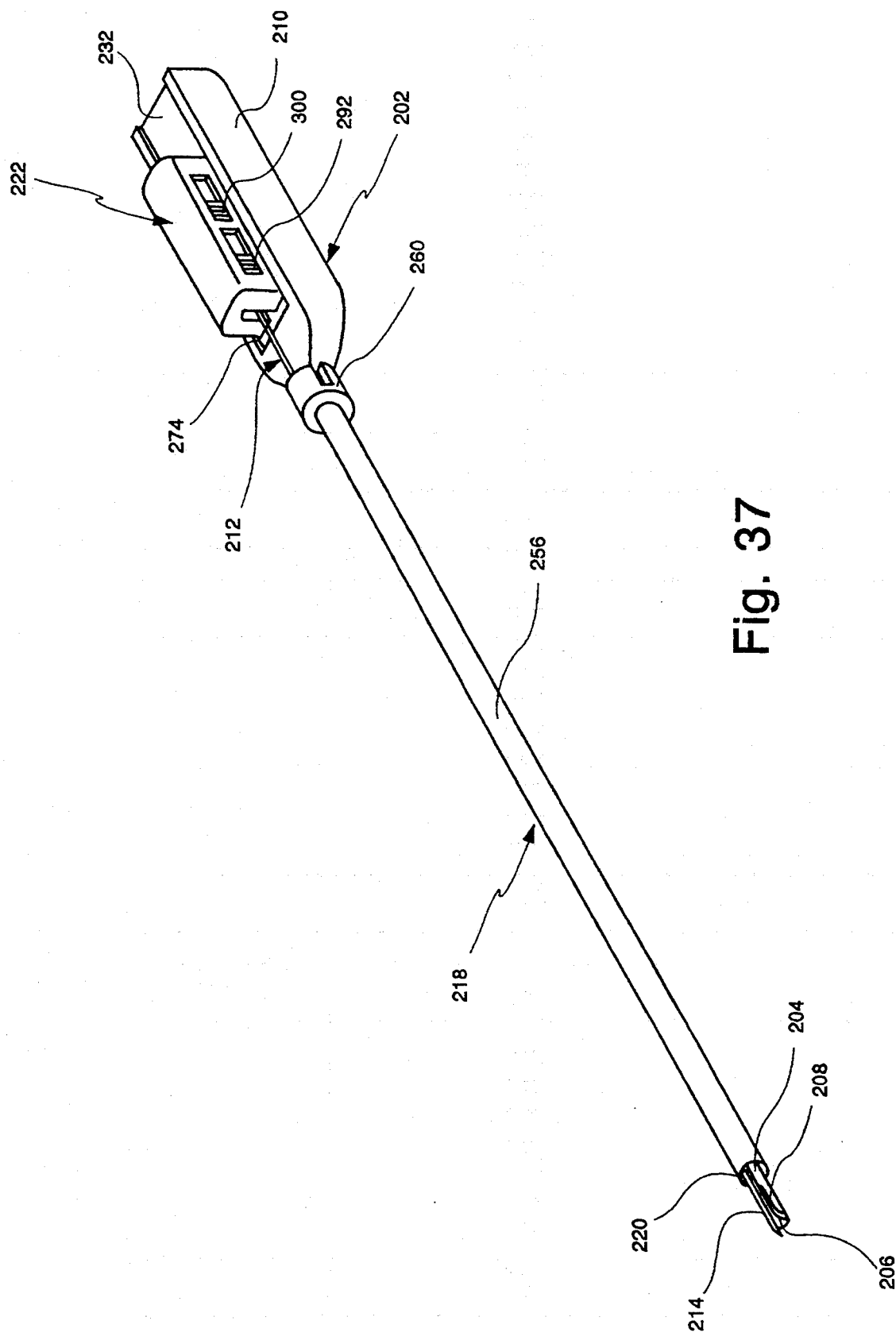
FIG. 37 is a perspective view of an assembled medical surgical apparatus including an ultrasonic imaging probe, a rigid sheath and a biopsy actuator.

Referring to FIG. 37, the assembled medical endosurgical apparatus 200 is shown in perspective. The medical endosurgical apparatus 200 includes the ultrasonic imaging probe 202 having the ultrasonic device 208 located near the insertion tip 206 of the rod-shaped carrier 204. Disposed over the rod-shaped carrier 204 of the ultrasonic imaging probe 202 is the rigid sheath 218 which engages the raised lip 234 of the probe handle 210 with the connecting clip 260. The engaging surfaces of the probe handle 210 and rigid sheath 218 are keyed to orient the lumen 220 of the rigid sheath 218 such that the needle sampling tips 214 of the biopsy needle assembly 212 passing through the lumen 220 are positioned within the field of view of the ultrasonic device 208.

The biopsy actuator 222 is slidably mounted on the probe handle 210 by engaging the rail 274 of the biopsy actuator 222 with the corresponding slot 232 on the probe handle 210. As mounted, the probe handle 210 and the biopsy actuator 222 together have a generally rounded contour for easy grasping and manipulation of both with one hand by a surgeon. The needle hubs 246 and 250 of the biopsy needle assembly 212 are disposed in their respective slides in the biopsy actuator 222 and the cannula 240 and the stylet 242 pass through the opening 290 in the wall of the actuator 222. The biopsy actuator 222 can be cocked using the pair of cannula cocking grips 292 and the pair of stylet cocking grips 300 mounted on opposite sides of the biopsy actuator 222. A biopsy of tissue near the insertion tip 206 of the ultrasonic imaging probe 202 can be taken by firing the biopsy actuator 222, to propel the needle sampling tips 214 of the biopsy needle assembly 212 in phased sequence to first pierce the tissue of interest and to then sever a sample of the tissue for collection.

The present invention also includes a method for locating tissue of interest inside of a body cavity and taking a biopsy sample of that tissue of interest. The method includes fitting the ultrasonic imaging probe 202 with the rigid sheath 218. The rod-shaped carrier 204 of the ultrasonic imaging probe 202 and a first portion 256 of the rigid sheath 218 are then inserted into the patient's body by a surgeon grasping the probe handle 210. The surgeon then manipulates the ultrasonic imaging probe 202, and thereby manipulates the ultrasonic device 208, to ultrasonically image tissue within the patient's body. When the tissue of interest is identified, then the biopsy actuator 222 is fitted with the biopsy needle assembly 212 and is mounted on the probe handle 210 such that the needle sampling tips 214 of the biopsy needle assembly 212 pass through the lumen 220 of the rigid sheath 218 and exit the lumen 220 with the needle sampling tips 214 positioned within the field of view of the ultrasonic device 208. The surgeon then cocks the biopsy actuator 222 using the cannula cocking grips 292 and the stylet cocking grips 300. Checking to see that both the needle sampling tips 214 and the tissue of interest are properly oriented to one another within the field of view of the ultrasonic device 208, then the surgeon can pivot the safety cover 316 to the "off-safety" position and also lock the biopsy actuator 222 in position relative to the probe handle 210. The surgeon can then fire the biopsy actuator 222 to effect taking of the biopsy sample with the needle sampling tips 214 by pressing the firing button 308. The safety cover 316 can then be closed, thereby releasing the biopsy actuator 222 from its locked position to the probe handle 210. The surgeon can then slidably remove the biopsy actuator 222 from the probe handle 210, and thereby extract the biopsy needle assembly 212 from the patient's body along with the tissue sample taken. Alternatively, the surgeon can remove the entire medical endosurgical apparatus 200, including the biopsy needle assembly 212, and the tissue sample can be recovered from the removed medical endosurgical apparatus 200.

Preferred embodiments for the ultrasonic imaging probe, rigid sheath and biopsy actuator have been described herein. It should be recognized, however, that the present invention is not so limited. Engagement structure for engaging the rigid sheath and the ultrasonic imaging probe can be any structures, having any keyed engaging shapes, capable of holding the rigid sheath and the ultrasonic imaging probe together and properly aligning the rigid sheath to the ultrasonic imaging probe. Interconnection between the probe handle of the ultrasonic imaging probe and the biopsy actuator can be by any mechanism capable of holding the probe handle and the biopsy actuator together and aligning the biopsy actuator and a biopsy collection device exiting the biopsy actuator with the field of view of the ultrasonic device on the ultrasonic imaging probe. Any biopsy collection device capable of being situated by a biopsy actuator mounted on the probe handle can be used with the medical endosurgical apparatus of the present invention.

The foregoing description of the invention has been presented for purposes of illustration and description. Further, the description is not intended to limit the variations and modifications commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternate embodiments to the extent permitted by the prior art.

What is claimed is:

1. A medical endosurgical apparatus having ultrasonic imaging and biopsy capabilities, the apparatus comprising:
   an endosurgical ultrasonic imaging probe having a first portion that has a first shape which facilitates insertion thereof, during use, through a surgical port and into a body cavity, and a second portion that has a second shape which substantially prevents insertion thereof, during use, through the surgical port and that remains outside of the body cavity, said first portion including ultrasonic means for receiving an ultrasonic signal and generating an electrical signal that is representative of the received ultrasonic signal and which may be used to prepare an image of tissue within the body cavity, said second portion including a probe handle for manipulating the probe, wherein said probe handle, due to said second shape, is substantially prevented from being inserted, during use, through said surgical port and remains outside the body cavity;
   biopsy actuator means for actuating a biopsy collection device that collects a tissue sample inside the body cavity; and
   means for facilitating readily physically interconnecting and readily physically disconnecting said probe handle and said biopsy actuator means so that said endosurgical ultrasonic imaging probe can be used with or without said biopsy actuator means and, when used with said biopsy actuator means, forms an integrated unit.

2. A medical endosurgical apparatus, as claimed in claim 1, wherein:
   said first portion comprises a first terminal end that is operatively connected to said second portion and a second terminal end that is inserted through the surgical port during use;
   wherein said first portion has a substantially circular cross-section located between said first terminal end and said second terminal end; and
   wherein cross-sections of said first portion at locations extending from said second terminal end towards said first terminal end are less than or equal to said substantially circular cross-section to facilitate use with a surgical port.

3. A medical endosurgical apparatus, as claimed in claim 2, wherein:
   said substantially circular cross-section has a diameter of less than about 10 millimeters.

4. A medical endosurgical apparatus, as claimed in claim 1, wherein:
   said ultrasonic means includes an array of ultrasonic transducers.

5. A medical endosurgical apparatus, as claimed in claim 1, wherein:
   said ultrasonic means including an array of ultrasonic transducers with a first portion of said array of transducers arranged in a substantially linear fashion with respect to one another and a second portion of said array of transducers arranged in a curve with respect to one another.

6. A medical endosurgical apparatus, as claimed in claim 1, wherein:
   said second portion includes a raised lip for use in holding a sheath disposed over said first portion of said endosurgical ultrasonic imaging probe in place.

7. A medical endosurgical apparatus, as claimed in claim 6, further comprising:
   a sheath for covering said first portion of said endosurgical ultrasonic imaging probe and including means for engaging said raised lip.

8. A medical endosurgical apparatus, as claimed in claim 7, wherein:
   said sheath is designed for disposal after a single use.

9. A medical endosurgical apparatus, as claimed in claim 1, wherein:
   said second portion includes a raised lip for holding a sheath disposed over said first portion of said endosurgical ultrasonic imaging probe in place, and includes a keyed shape that is used to orient the sheath relative to the endosurgical ultrasonic imaging probe.

10. A medical endosurgical apparatus, as claimed in claim 9, wherein:
    said keyed shape includes a curved portion and a substantially straight portion.

11. A medical endosurgical apparatus, as claimed in claim 1, wherein:

said means for facilitating readily physically interconnecting and readily physically disconnecting includes a slot located on one of said probe handle and said biopsy actuator means, and a rail located on the other of said probe handle and said biopsy actuator means and capable of matingly engaging said slot.

12. A medical endosurgical apparatus, as claimed in claim 1, wherein:
said means for facilitating readily physically interconnecting and readily physically disconnecting includes means for permitting said biopsy actuator means to be moved relative to said probe handle so that the biopsy collection device can be moved to sample the appropriate tissue.

13. A medical endosurgical apparatus, as claimed in claim 1, wherein:
said means for facilitating readily physically interconnecting and readily physically disconnecting includes means for permitting said biopsy actuator means to be moved relative to said probe handle when interconnected, so that the biopsy collection device can be moved to sample the appropriate tissue and means for fixing the position of said biopsy actuator means relative to said probe handle so that the biopsy collection device samples the appropriate tissue.

14. A medical endosurgical apparatus, as claimed in claim 1, wherein:
said probe handle includes a longitudinally extending curved portion and a longitudinally extending, substantially flat portion;
wherein said means for facilitating readily physically interconnecting and readily physically disconnecting positions said biopsy actuator means adjacent to said longitudinally extending, substantially flat portion of said probe handle;
wherein said curved portion facilitates grasping of both said probe handle and said biopsy actuator means.

15. A medical endosurgical apparatus, as claimed in claim 1, wherein:
said biopsy actuator means includes means for cocking a carrier that moves at least a portion of the biopsy collection device, said means for cocking including opposing grips mounted on opposing surfaces of said biopsy actuator means to facilitate cocking of the biopsy actuator means.

16. A medical endosurgical apparatus, as claimed in claim 1, wherein:
said biopsy actuator means includes a first means for displacing a first portion of the biopsy collection device and a second means for displacing a second portion of the biopsy collection device that is different than said first portion of the biopsy collection device.

17. A medical endosurgical apparatus, as claimed in claim 1, wherein:
said means for facilitating readily physically interconnecting and readily physically disconnecting includes means for orienting said biopsy actuator means so that the biopsy collection device can be positioned in the field of view of said ultrasonic means.

18. A medical endosurgical apparatus, as claimed in claim 1, wherein:
said means for facilitating readily physically interconnecting and readily physically disconnecting includes means for slidably interconnecting and disconnecting said biopsy actuator means and said probe handle.

19. A medical endosurgical apparatus, as claimed in claim 1, further comprising:
a sheath for covering said first portion of said endosurgical ultrasonic imaging probe, said sheath having a cross-sectional shape suitable for insertion through a surgical port.

20. A medical endosurgical apparatus, as claimed in claim 1, further comprising:
a sheath for covering said first portion of said endosurgical ultrasonic imaging probe; and
means for retaining said sheath to said endosurgical ultrasonic imaging probe to prevent displacement of said sheath during use.

21. A medical endosurgical apparatus, as claimed in claim 1, further comprising:
a sheath for covering said first portion of said endosurgical ultrasonic imaging probe that includes a lumen for receiving a biopsy collection device, wherein said lumen has an exit port; and
said biopsy actuator means includes means for moving at least a portion of the biopsy collection device beyond said exit port.

22. A medical endosurgical apparatus having ultrasonic imaging and biopsy capabilities, the apparatus comprising:
an endosurgical ultrasonic imaging probe having a first portion designed for insertion, during use, into a body through a surgical port and a second portion designed for remaining outside of the body cavity during use, said first portion including ultrasonic means for receiving an ultrasonic signal and generating an electrical signal that is representative of the received ultrasonic signal and which may be used to prepare an image of tissue within the body cavity, said second portion including a probe handle for manipulating the probe;
biopsy actuator means for actuating a biopsy collection device that collects a tissue sample inside the body cavity;
means for physically interconnecting with said probe handle and said biopsy actuator means;
said second portion includes a raised lip for holding a sheath disposed over said first portion of said endosurgical ultrasonic imaging probe in place, and includes a keyed shape that is used to orient a sheath relative to the endosurgical ultrasonic imaging probe; and
a sheath for covering said first portion of said endosurgical ultrasonic imaging probe, said sheath includes a lumen for receiving a biopsy collection device and means for engaging said raised lip to hold said sheath in place relative to the endosurgical ultrasonic imaging probe, said means for engaging having a complementary keyed shape to said keyed shape of said endosurgical ultrasonic imaging probe so that, upon engagement of said raised lip and said means for engaging, said lumen is oriented so that the biopsy collection device can be disposed in the field of view of the ultrasonic means.

23. A medical endosurgical apparatus, as claimed in claim 22, wherein:
said sheath having a cross-sectional shape suitable for insertion through a surgical port.

24. A medical endosurgical apparatus having ultrasonic imaging and biopsy capabilities, the apparatus comprising:
   an endosurgical ultrasonic imaging probe having a first portion designed for insertion, during use, into a body through a surgical port and a second portion designed for remaining outside of the body cavity during use, said first portion including ultrasonic means for receiving an ultrasonic signal and generating an electrical signal that is representative of the received ultrasonic signal and which may be used to prepare an image of tissue within the body cavity, said second portion including a probe handle for manipulating the probe;
   biopsy actuator means for actuating a biopsy collection device that collects a tissue sample inside the body cavity;
   means for physically interconnecting with said probe handle and said biopsy actuator means; and
   a sheath for covering said first portion of said endosurgical ultrasonic imaging probe and including a lumen for receiving a biopsy collection device that is actuated by said biopsy actuator means.

25. A medical endosurgical apparatus, as claimed in claim 24, wherein:
   said biopsy actuator means includes a first means for displacing a first portion of the biopsy collection device and a second means for displacing a second portion of the biopsy collection device that is different than said first portion of the biopsy collection device.

26. A medical endosurgical apparatus, as claimed in claim 24, wherein:
   said means for physically interconnecting includes means for orienting said biopsy actuator means so that the biopsy collection device can be positioned in the field of view of said ultrasonic means.

27. A medical endosurgical apparatus, as claimed in claim 24, wherein:
   said means for physically interconnecting includes means for permitting a location of said biopsy actuator means relative to said probe handle to be changed and thereby, when in use, permit a location of the biopsy collection device relative to said ultrasonic means to be changed.

28. A medical endosurgical apparatus, as claimed in claim 27, wherein:
   said means for physically interconnecting includes means for fixing the location of said biopsy actuator means relative to said probe handle.

29. A medical endosurgical apparatus, as claimed in claim 24, wherein:
   said sheath having a cross-sectional shape suitable for insertion through a surgical port.

30. A medical endosurgical apparatus, as claimed in claim 24, further comprising:
   means for retaining said sheath to said endosurgical ultrasonic imaging probe to prevent displacement of said sheath during use.

31. A medical endosurgical apparatus, as claimed in claim 24, further comprising:
   means for orienting said sheath relative to said endosurgical ultrasonic imaging probe so that, when a biopsy collection device is located in said lumen, the biopsy collection device can be positioned in the field of view of said ultrasonic means.

32. A medical endosurgical apparatus having ultrasonic imaging and biopsy capabilities, the apparatus comprising:
   an endosurgical ultrasonic imaging probe having a first portion that has a first shape which facilitates insertion thereof, during use, through a surgical port and into a body cavity, and a second portion that has a second shape which substantially prevents insertion thereof, during use, through the surgical port and that remains outside of the body cavity, said first portion including ultrasonic means for receiving an ultrasonic signal and generating an electrical signal that is representative of the received ultrasonic signal and which may be used to prepare an image of tissue within the body cavity, said second portion including a probe handle for manipulating the probe, wherein Said probe handle, due to said second shape, is substantially prevented from being inserted, during use, through said surgical port and remains outside the body cavity;
   wherein said second portion of said probe includes means for facilitating readily engaging and readily disengaging one of the following: a sheath that can be disposed over said first portion of said ultrasonic imaging probe or a biopsy actuator means for actuating a biopsy collection device.

33. A medical endosurgical apparatus, as claimed in claim 32, wherein:
   means for facilitating readily engaging and readily disengaging includes one of the following: a groove or a rail for engaging a biopsy actuator means.

34. A medical endosurgical apparatus as claimed in claim 32, wherein:
   said means for facilitating readily engaging and readily disengaging includes a raised lip for engaging a sheath.

35. A medical endosurgical apparatus having ultrasonic and biopsy capabilities, the apparatus comprising:
   an endosurgical ultrasonic imaging probe having a first portion that has a first shape which facilitates insertion thereof, during use, through a surgical port and into a body cavity, and a second portion that has a second shape which substantially prevents insertion thereof, during use, through the surgical port and therefore remains outside of the body cavity, said first portion including ultrasonic means for receiving an ultrasonic signal and generating an electrical signal that is representative of the received ultrasonic signal and which may be used to prepare an image of tissue within the body cavity, said second portion including a probe handle for manipulating the probe, wherein said probe handle, due to said second shape, is substantially prevented from being inserted, during use, through said surgical port and therefore remains outside the body cavity;
   biopsy actuator means for actuating a biopsy collection device that collects a tissue sample inside the body cavity;
   means for facilitating readily physically interconnecting and readily physically disconnecting said probe handle and said biopsy actuator means so that said endosurgical ultrasonic imaging probe can be used with or without said biopsy actuator means and, when used with said biopsy actuator means, forms an integrated unit;

wherein said means for facilitating readily physically interconnecting and readily physically disconnecting includes means for orienting said biopsy actuator means to said endosurgical ultrasonic imaging probe so that the biopsy collection device can be positioned in the field of view of said ultrasonic means;

wherein said means for facilitating readily physically interconnecting and readily physically disconnecting includes means for permitting a location of said biopsy actuator means relative to said probe handle to be changed and thereby, when in use, permit a location of the biopsy collection device relative to said ultrasonic means to be changed;

wherein said means for facilitating readily physically interconnecting and readily physically disconnecting includes means for fixing the location of said biopsy actuator means relative to said probe handle;

a sheath for covering said first portion of said ultrasonic imaging probe;

wherein said sheath has a cross-sectional shape suitable for insertion through a surgical port;

wherein said sheath includes a lumen for receiving the biopsy collection device that is actuated by said biopsy actuator means;

means for retaining said sheath to said endosurgical ultrasonic imaging probe to prevent displacement of said sheath during use; and means for orienting said sheath relative to said endosurgical ultrasonic imaging probe so that, when a biopsy collection device is located in said lumen, the biopsy collection device can be positioned in the field of view of said ultrasonic means.

* * * * *